(12) United States Patent  
Perry et al.

(10) Patent No.: US 9,327,100 B2
(45) Date of Patent: *May 3, 2016

(54) SELECTIVE DRUG DELIVERY IN A LUMEN

(71) Applicant: VESSIX VASCULAR, INC., Laguna Hills, CA (US)

(72) Inventors: Michael Perry, Los Altos, CA (US); Corbett W. Stone, San Diego, CA (US); Rolfe Tyson Gustus, San Jose, CA (US); Ronda Schreiber, Poway, CA (US); Meital Mazor, Carlsbad, CA (US); Brian D. Conn, San Diego, CA (US)

(73) Assignee: VESSIX VASCULAR, INC., Laguna Hills, CA (US)

( * ) Notice: Subject to any disclaimer, the term of this patent is extended or adjusted under 35 U.S.C. 154(b) by 170 days.

This patent is subject to a terminal disclaimer.

(21) Appl. No.: 13/796,777

(22) Filed: Mar. 12, 2013

(65) Prior Publication Data

US 2013/0172815 A1 Jul. 4, 2013

Related U.S. Application Data

(63) Continuation of application No. 12/616,720, filed on Nov. 11, 2009, now Pat. No. 8,396,548.

(60) Provisional application No. 61/114,958, filed on Nov. 14, 2008.

(51) Int. Cl.
*A61M 25/10* (2013.01)
*A61B 5/053* (2006.01)
(Continued)

(52) U.S. Cl.
CPC ............... *A61M 25/10* (2013.01); *A61B 5/053* (2013.01); *A61B 5/6853* (2013.01);
(Continued)

(58) Field of Classification Search
CPC ............... A61M 2025/0057; A61M 2025/105; A61M 2025/1075
USPC ................... 600/381; 604/20, 21, 53, 96, 99, 604/103.01–103.11, 265, 266; 606/27, 32, 606/192, 194
See application file for complete search history.

(56) References Cited

U.S. PATENT DOCUMENTS 164,184 A 6/1875 Jeeome
1,167,014 A 1/1916 O'Brien
(Continued)

FOREIGN PATENT DOCUMENTS

CA 2384866 A1 5/2001
CN 101583323 A 11/2009
(Continued)

OTHER PUBLICATIONS

Van Den Berg, "Light echoes image the human body," OLE, Oct. 2001, p. 35-37.
(Continued)

*Primary Examiner* — Gerald Landry, II
(74) *Attorney, Agent, or Firm* — Seager, Tufte & Wickhem, LLP

(57) ABSTRACT

Methods and systems are disclosed for selective drug or fluid delivery in a lumen through a coating or fluid delivery channels. One system includes an elongate catheter having a proximal end and a distal end with an axis therebetween, the catheter having a radially expandable balloon near the distal end and an energy delivery portion proximate the balloon for transmission of energy, a thermally changeable coating having a releasable drug coupled to the balloon, the thermally changeable coating being oriented to be urged against the body tissue when the expandable balloon expands and an energy source operatively coupled to the energy delivery portion configured to energize the energy delivery portion to heat and liquefy the thermally changeable coating to release the drug to the body tissue.

19 Claims, 4 Drawing Sheets

(51) Int. Cl.
| | |
|---|---|
| *A61B 5/00* | (2006.01) |
| *A61B 18/14* | (2006.01) |
| *A61L 29/08* | (2006.01) |
| *A61L 29/14* | (2006.01) |
| *A61L 29/16* | (2006.01) |
| *A61B 18/24* | (2006.01) |
| *A61B 18/00* | (2006.01) |
| *A61B 18/18* | (2006.01) |
| *A61M 37/00* | (2006.01) |
| *A61N 7/02* | (2006.01) |

(52) U.S. Cl.
CPC ............ *A61B 18/1492* (2013.01); *A61L 29/08* (2013.01); *A61L 29/14* (2013.01); *A61L 29/16* (2013.01); *A61M 25/104* (2013.01); *A61B 18/24* (2013.01); *A61B 2018/0022* (2013.01); *A61B 2018/00154* (2013.01); *A61B 2018/00214* (2013.01); *A61B 2018/00898* (2013.01); *A61B 2018/1861* (2013.01); *A61L 2300/45* (2013.01); *A61L 2300/606* (2013.01); *A61M 37/0092* (2013.01); *A61M 2025/105* (2013.01); *A61M 2025/1086* (2013.01); *A61M 2025/1088* (2013.01); *A61N 7/022* (2013.01)

(56) References Cited

U.S. PATENT DOCUMENTS

| | | | |
|---|---|---|---|
| 2,505,358 A | 4/1950 | Gusberg et al. |
| 2,701,559 A | 2/1955 | Cooper |
| 3,108,593 A | 10/1963 | Glassman |
| 3,108,594 A | 10/1963 | Glassman |
| 3,540,431 A | 11/1970 | Mobin |
| 3,952,747 A | 4/1976 | Kimmell |
| 3,996,938 A | 12/1976 | Clark, III |
| 4,046,150 A | 9/1977 | Schwartz et al. |
| 4,290,427 A | 9/1981 | Chin |
| 4,402,686 A | 9/1983 | Medel |
| 4,483,341 A | 11/1984 | Witteles et al. |
| 4,574,804 A | 3/1986 | Kurwa |
| 4,587,975 A | 5/1986 | Salo et al. |
| 4,649,936 A | 3/1987 | Ungar et al. |
| 4,682,596 A | 7/1987 | Bales et al. |
| 4,709,698 A | 12/1987 | Johnston et al. |
| 4,765,331 A | 8/1988 | Petruzzi et al. |
| 4,770,653 A | 9/1988 | Shturman |
| 4,784,132 A | 11/1988 | Fox et al. |
| 4,784,162 A | 11/1988 | Ricks et al. |
| 4,785,806 A | 11/1988 | Deckelbaum et al. |
| 4,788,975 A | 12/1988 | Shturman et al. |
| 4,790,310 A | 12/1988 | Ginsburg et al. |
| 4,799,479 A | 1/1989 | Spears |
| 4,823,791 A | 4/1989 | D'Amelio et al. |
| 4,830,003 A | 5/1989 | Wolff et al. |
| 4,849,484 A | 7/1989 | Heard |
| 4,862,886 A | 9/1989 | Clarke et al. |
| 4,887,605 A | 12/1989 | Angelsen et al. |
| 4,920,979 A | 5/1990 | Bullara |
| 4,938,766 A | 7/1990 | Jarvik |
| 4,955,377 A | 9/1990 | Lennox et al. |
| 4,976,711 A | 12/1990 | Parins et al. |
| 5,034,010 A | 7/1991 | Kittrell et al. |
| 5,052,402 A | 10/1991 | Bencini et al. |
| 5,053,033 A | 10/1991 | Clarke et al. |
| 5,071,424 A | 12/1991 | Reger et al. |
| 5,074,871 A | 12/1991 | Groshong et al. |
| 5,098,429 A | 3/1992 | Sterzer et al. |
| 5,098,431 A | 3/1992 | Rydell |
| 5,102,402 A | 4/1992 | Dror et al. |
| RE33,925 E | 5/1992 | Bales et al. |
| 5,109,859 A | 5/1992 | Jenkins |
| 5,125,928 A | 6/1992 | Parins et al. |
| 5,129,396 A | 7/1992 | Rosen et al. |
| 5,139,496 A | 8/1992 | Hed |
| 5,143,836 A | 9/1992 | Hartman et al. |
| 5,156,610 A | 10/1992 | Reger et al. |
| 5,158,564 A | 10/1992 | Schnepp-Pesch |
| 5,170,802 A | 12/1992 | Mehra |
| 5,178,620 A | 1/1993 | Eggers et al. |
| 5,178,625 A | 1/1993 | Groshong et al. |
| 5,190,540 A | 3/1993 | Lee |
| 5,211,651 A | 5/1993 | Reger et al. |
| 5,234,407 A | 8/1993 | Teirstein et al. |
| 5,242,441 A | 9/1993 | Avitall |
| 5,251,634 A | 10/1993 | Weinberg et al. |
| 5,255,679 A | 10/1993 | Imran |
| 5,263,493 A | 11/1993 | Avitall |
| 5,267,954 A | 12/1993 | Nita et al. |
| 5,277,201 A | 1/1994 | Stern et al. |
| 5,282,484 A | 2/1994 | Reger et al. |
| 5,286,254 A | 2/1994 | Shapland et al. |
| 5,295,484 A | 3/1994 | Marcus |
| 5,297,564 A | 3/1994 | Love et al. |
| 5,300,068 A | 4/1994 | Rosar et al. |
| 5,301,683 A | 4/1994 | Durkan |
| 5,304,115 A | 4/1994 | Pflueger et al. |
| 5,304,121 A | 4/1994 | Sahatjian |
| 5,304,171 A | 4/1994 | Gregory et al. |
| 5,304,173 A | 4/1994 | Kittrell et al. |
| 5,306,250 A | 4/1994 | March et al. |
| 5,312,328 A | 5/1994 | Nita et al. |
| 5,314,466 A | 5/1994 | Stern et al. |
| 5,322,064 A | 6/1994 | Lundquist |
| 5,324,255 A | 6/1994 | Passafaro et al. |
| 5,326,341 A | 7/1994 | Lew et al. |
| 5,326,342 A | 7/1994 | Pflueger et al. |
| 5,330,518 A | 7/1994 | Neilson et al. |
| 5,333,614 A | 8/1994 | Feiring |
| 5,342,292 A | 8/1994 | Nita et al. |
| 5,344,395 A | 9/1994 | Whalen et al. |
| 5,364,392 A | 11/1994 | Warner et al. |
| 5,365,172 A | 11/1994 | Hrovat et al. |
| 5,368,557 A | 11/1994 | Nita et al. |
| 5,368,558 A | 11/1994 | Nita et al. |
| 5,380,274 A | 1/1995 | Nita et al. |
| 5,380,319 A | 1/1995 | Saito et al. |
| 5,382,228 A | 1/1995 | Nita et al. |
| 5,383,874 A | 1/1995 | Jackson et al. |
| 5,383,917 A | 1/1995 | Desai et al. |
| 5,397,301 A | 3/1995 | Pflueger et al. |
| 5,397,339 A | 3/1995 | Desai |
| 5,401,272 A | 3/1995 | Perkins et al. |
| 5,403,311 A | 4/1995 | Abele et al. |
| 5,405,318 A | 4/1995 | Nita et al. |
| 5,405,346 A | 4/1995 | Grundy et al. |
| 5,409,000 A | 4/1995 | Imran |
| 5,417,672 A | 5/1995 | Nita et al. |
| 5,419,767 A | 5/1995 | Eggers et al. |
| 5,427,118 A | 6/1995 | Nita et al. |
| 5,432,876 A | 7/1995 | Appeldorn et al. |
| 5,441,498 A | 8/1995 | Perkins et al. |
| 5,447,509 A | 9/1995 | Mills et al. |
| 5,451,207 A | 9/1995 | Yock |
| 5,453,091 A | 9/1995 | Taylor et al. |
| 5,454,788 A | 10/1995 | Walker et al. |
| 5,454,809 A | 10/1995 | Janssen |
| 5,455,029 A | 10/1995 | Hartman et al. |
| 5,456,682 A | 10/1995 | Edwards et al. |
| 5,457,042 A | 10/1995 | Hartman et al. |
| 5,471,982 A | 12/1995 | Edwards et al. |
| 5,474,530 A | 12/1995 | Passafaro et al. |
| 5,478,351 A | 12/1995 | Meade et al. |
| 5,496,311 A | 3/1996 | Abele et al. |
| 5,496,312 A | 3/1996 | Klicek et al. |
| 5,498,261 A | 3/1996 | Strul |
| 5,505,201 A | 4/1996 | Grill et al. |
| 5,505,730 A | 4/1996 | Edwards |
| 5,507,744 A | 4/1996 | Tay et al. |
| 5,522,873 A | 6/1996 | Jackman et al. |
| 5,531,520 A | 7/1996 | Grimson et al. |
| 5,540,656 A | 7/1996 | Pflueger et al. |
| 5,540,679 A | 7/1996 | Fram et al. |
| 5,540,681 A | 7/1996 | Strul et al. |

(56) References Cited

U.S. PATENT DOCUMENTS

| | | | |
|---|---|---|---|
| 5,542,917 A | 8/1996 | Nita et al. | |
| 5,545,161 A | 8/1996 | Imran | |
| 5,562,100 A | 10/1996 | Kittrell et al. | |
| 5,571,122 A | 11/1996 | Kelly et al. | |
| 5,571,151 A | 11/1996 | Gregory | |
| 5,573,531 A | 11/1996 | Gregory et al. | |
| 5,573,533 A | 11/1996 | Strul | |
| 5,584,831 A | 12/1996 | McKay | |
| 5,584,872 A | 12/1996 | Lafontaine et al. | |
| 5,588,962 A * | 12/1996 | Nicholas et al. | 604/507 |
| 5,599,346 A | 2/1997 | Edwards et al. | |
| 5,601,526 A | 2/1997 | Chapelon et al. | |
| 5,609,606 A | 3/1997 | O'Boyle et al. | |
| 5,626,576 A | 5/1997 | Janssen | |
| 5,630,837 A | 5/1997 | Crowley | |
| 5,637,090 A | 6/1997 | McGee et al. | |
| 5,643,255 A | 7/1997 | Organ | |
| 5,643,297 A | 7/1997 | Nordgren et al. | |
| 5,647,847 A | 7/1997 | Lafontaine et al. | |
| 5,649,923 A | 7/1997 | Gregory et al. | |
| 5,651,780 A | 7/1997 | Jackson et al. | |
| 5,653,684 A | 8/1997 | Laptewicz et al. | |
| 5,662,671 A | 9/1997 | Barbut et al. | |
| 5,665,062 A | 9/1997 | Houser | |
| 5,665,098 A | 9/1997 | Kelly et al. | |
| 5,666,964 A | 9/1997 | Meilus | |
| 5,667,490 A | 9/1997 | Keith et al. | |
| 5,672,174 A | 9/1997 | Gough et al. | |
| 5,676,693 A | 10/1997 | Lafontaine | |
| 5,678,296 A | 10/1997 | Fleischhacker et al. | |
| 5,681,282 A | 10/1997 | Eggers et al. | |
| RE35,656 E | 11/1997 | Feinberg | |
| 5,688,266 A | 11/1997 | Edwards et al. | |
| 5,693,015 A | 12/1997 | Walker et al. | |
| 5,693,029 A | 12/1997 | Leonhardt et al. | |
| 5,693,043 A | 12/1997 | Kittrell et al. | |
| 5,693,082 A | 12/1997 | Warner et al. | |
| 5,695,504 A | 12/1997 | Gifford et al. | |
| 5,697,369 A | 12/1997 | Long, Jr. et al. | |
| 5,697,909 A | 12/1997 | Eggers et al. | |
| 5,702,386 A | 12/1997 | Stern et al. | |
| 5,702,433 A | 12/1997 | Taylor et al. | |
| 5,706,809 A | 1/1998 | Littmann et al. | |
| 5,713,942 A | 2/1998 | Stern et al. | |
| 5,715,819 A | 2/1998 | Svenson et al. | |
| 5,735,846 A | 4/1998 | Panescu et al. | |
| 5,741,214 A | 4/1998 | Ouchi et al. | |
| 5,741,248 A | 4/1998 | Stern et al. | |
| 5,741,249 A | 4/1998 | Moss et al. | |
| 5,743,903 A | 4/1998 | Stern et al. | |
| 5,748,347 A | 5/1998 | Erickson | |
| 5,749,914 A | 5/1998 | Janssen | |
| 5,755,682 A | 5/1998 | Knudson et al. | |
| 5,755,715 A | 5/1998 | Stern et al. | |
| 5,755,753 A | 5/1998 | Knowlton et al. | |
| 5,769,847 A | 6/1998 | Panescu et al. | |
| 5,769,880 A | 6/1998 | Truckai et al. | |
| 5,775,338 A | 7/1998 | Hastings | |
| 5,776,174 A | 7/1998 | Van Tassel | |
| 5,779,698 A | 7/1998 | Clayman et al. | |
| 5,782,760 A | 7/1998 | Schaer | |
| 5,785,702 A | 7/1998 | Murphy et al. | |
| 5,792,105 A | 8/1998 | Lin et al. | |
| 5,797,849 A | 8/1998 | Vesely et al. | |
| 5,797,903 A | 8/1998 | Swanson et al. | |
| 5,800,484 A | 9/1998 | Gough et al. | |
| 5,800,494 A | 9/1998 | Campbell et al. | |
| 5,807,306 A | 9/1998 | Shapland et al. | |
| 5,810,802 A | 9/1998 | Panescu et al. | |
| 5,810,803 A | 9/1998 | Moss et al. | |
| 5,810,810 A | 9/1998 | Tay et al. | |
| 5,817,092 A | 10/1998 | Behl | |
| 5,817,113 A | 10/1998 | Gifford et al. | |
| 5,817,144 A | 10/1998 | Gregory | |
| 5,823,956 A | 10/1998 | Roth et al. | |
| 5,827,203 A | 10/1998 | Nita et al. | |
| 5,827,268 A | 10/1998 | Laufer | |
| 5,829,447 A | 11/1998 | Stevens et al. | |
| 5,830,213 A | 11/1998 | Panescu et al. | |
| 5,830,222 A | 11/1998 | Makower | |
| 5,832,228 A | 11/1998 | Holden et al. | |
| 5,833,593 A | 11/1998 | Liprie | |
| 5,836,874 A | 11/1998 | Swanson et al. | |
| 5,840,076 A | 11/1998 | Swanson et al. | |
| 5,843,016 A | 12/1998 | Lugnani et al. | |
| 5,846,238 A | 12/1998 | Jackson et al. | |
| 5,846,239 A | 12/1998 | Swanson et al. | |
| 5,846,245 A | 12/1998 | McCarthy et al. | |
| 5,848,969 A | 12/1998 | Panescu et al. | |
| 5,853,411 A | 12/1998 | Whayne et al. | |
| 5,855,614 A | 1/1999 | Stevens et al. | |
| 5,860,974 A | 1/1999 | Abele | |
| 5,865,801 A | 2/1999 | Houser | |
| 5,868,735 A | 2/1999 | Lafontaine et al. | |
| 5,868,736 A | 2/1999 | Swanson et al. | |
| 5,869,127 A | 2/1999 | Zhong | |
| 5,871,483 A | 2/1999 | Jackson et al. | |
| 5,871,524 A | 2/1999 | Knowlton et al. | |
| 5,875,782 A | 3/1999 | Ferrari et al. | |
| 5,876,369 A | 3/1999 | Houser | |
| 5,876,374 A | 3/1999 | Alba et al. | |
| 5,876,397 A | 3/1999 | Edelman et al. | |
| 5,879,348 A | 3/1999 | Owens et al. | |
| 5,891,114 A | 4/1999 | Chien et al. | |
| 5,891,135 A | 4/1999 | Jackson et al. | |
| 5,891,136 A | 4/1999 | McGee et al. | |
| 5,891,138 A | 4/1999 | Tu et al. | |
| 5,895,378 A | 4/1999 | Nita | |
| 5,897,552 A | 4/1999 | Edwards et al. | |
| 5,902,328 A | 5/1999 | Lafontaine et al. | |
| 5,904,651 A | 5/1999 | Swanson et al. | |
| 5,904,667 A | 5/1999 | Falwell et al. | |
| 5,904,697 A | 5/1999 | Gifford et al. | |
| 5,904,709 A | 5/1999 | Arndt et al. | |
| 5,906,614 A | 5/1999 | Stern et al. | |
| 5,906,623 A | 5/1999 | Peterson | |
| 5,906,636 A | 5/1999 | Casscells et al. | |
| 5,916,192 A | 6/1999 | Nita et al. | |
| 5,916,227 A | 6/1999 | Keith et al. | |
| 5,916,239 A | 6/1999 | Geddes et al. | |
| 5,919,219 A | 7/1999 | Knowlton et al. | |
| 5,924,424 A | 7/1999 | Stevens et al. | |
| 5,925,038 A | 7/1999 | Panescu et al. | |
| 5,934,284 A | 8/1999 | Plaia et al. | |
| 5,935,063 A | 8/1999 | Nguyen | |
| 5,938,670 A | 8/1999 | Keith et al. | |
| 5,947,977 A | 9/1999 | Slepian et al. | |
| 5,948,011 A | 9/1999 | Knowlton et al. | |
| 5,951,494 A | 9/1999 | Wang et al. | |
| 5,951,539 A | 9/1999 | Nita et al. | |
| 5,954,717 A | 9/1999 | Behl et al. | |
| 5,957,882 A | 9/1999 | Nita et al. | |
| 5,957,941 A | 9/1999 | Ream et al. | |
| 5,957,969 A | 9/1999 | Warner et al. | |
| 5,961,513 A | 10/1999 | Swanson et al. | |
| 5,964,757 A | 10/1999 | Ponzi et al. | |
| 5,967,976 A | 10/1999 | Larsen et al. | |
| 5,967,978 A | 10/1999 | Littmann et al. | |
| 5,967,984 A | 10/1999 | Chu et al. | |
| 5,971,975 A | 10/1999 | Mills et al. | |
| 5,972,026 A | 10/1999 | Laufer et al. | |
| 5,980,563 A | 11/1999 | Tu et al. | |
| 5,989,208 A | 11/1999 | Nita et al. | |
| 5,989,284 A | 11/1999 | Laufer | |
| 5,993,462 A | 11/1999 | Pomeranz et al. | |
| 5,997,497 A | 12/1999 | Nita et al. | |
| 5,999,678 A | 12/1999 | Murphy et al. | |
| 6,004,269 A | 12/1999 | Crowley et al. | |
| 6,004,316 A | 12/1999 | Laufer et al. | |
| 6,007,514 A | 12/1999 | Nita | |
| 6,010,522 A | 1/2000 | Barbut et al. | |
| 6,013,033 A | 1/2000 | Berger et al. | |
| 6,014,590 A | 1/2000 | Whayne et al. | |
| 6,022,309 A | 2/2000 | Celliers et al. | |

(56) References Cited

U.S. PATENT DOCUMENTS

| | | |
|---|---|---|
| 6,024,740 A | 2/2000 | Lesh et al. |
| 6,030,611 A | 2/2000 | Gorecki et al. |
| 6,032,675 A | 3/2000 | Rubinsky et al. |
| 6,033,397 A | 3/2000 | Laufer et al. |
| 6,033,398 A | 3/2000 | Farley et al. |
| 6,036,687 A | 3/2000 | Laufer et al. |
| 6,036,689 A | 3/2000 | Tu et al. |
| 6,041,260 A | 3/2000 | Stern et al. |
| 6,050,994 A | 4/2000 | Sherman et al. |
| 6,056,744 A | 5/2000 | Edwards |
| 6,056,746 A | 5/2000 | Goble et al. |
| 6,063,085 A | 5/2000 | Tay et al. |
| 6,066,096 A | 5/2000 | Smith et al. |
| 6,066,139 A | 5/2000 | Ryan et al. |
| 6,068,638 A | 5/2000 | Makower |
| 6,068,653 A | 5/2000 | Lafontaine |
| 6,071,277 A | 6/2000 | Farley et al. |
| 6,071,278 A | 6/2000 | Panescu et al. |
| 6,078,839 A | 6/2000 | Carson |
| 6,079,414 A | 6/2000 | Roth |
| 6,080,171 A | 6/2000 | Keith et al. |
| 6,081,749 A | 6/2000 | Ingle et al. |
| 6,083,159 A | 7/2000 | Driscoll et al. |
| 6,086,581 A | 7/2000 | Reynolds et al. |
| 6,091,995 A | 7/2000 | Ingle et al. |
| 6,093,166 A | 7/2000 | Knudson et al. |
| 6,096,021 A | 8/2000 | Helm et al. |
| 6,099,526 A | 8/2000 | Whayne et al. |
| 6,102,908 A | 8/2000 | Tu et al. |
| 6,106,477 A | 8/2000 | Miesel et al. |
| 6,110,187 A | 8/2000 | Donlon et al. |
| 6,114,311 A | 9/2000 | Parmacek et al. |
| 6,117,101 A | 9/2000 | Diederich et al. |
| 6,117,128 A | 9/2000 | Gregory |
| 6,120,476 A | 9/2000 | Fung et al. |
| 6,120,516 A | 9/2000 | Selmon et al. |
| 6,121,775 A | 9/2000 | Pearlman |
| 6,123,679 A | 9/2000 | Lafaut et al. |
| 6,123,682 A | 9/2000 | Knudson et al. |
| 6,123,702 A | 9/2000 | Swanson et al. |
| 6,123,703 A | 9/2000 | Tu et al. |
| 6,123,718 A | 9/2000 | Tu et al. |
| 6,129,725 A | 10/2000 | Tu et al. |
| 6,135,997 A | 10/2000 | Laufer et al. |
| 6,142,991 A | 11/2000 | Schatzberger et al. |
| 6,142,993 A | 11/2000 | Whayne et al. |
| 6,149,647 A | 11/2000 | Tu et al. |
| 6,152,899 A | 11/2000 | Farley et al. |
| 6,152,912 A | 11/2000 | Jansen et al. |
| 6,156,046 A | 12/2000 | Passafaro et al. |
| 6,158,250 A | 12/2000 | Tibbals et al. |
| 6,159,187 A | 12/2000 | Park et al. |
| 6,159,225 A | 12/2000 | Makower |
| 6,161,048 A | 12/2000 | Sluijter et al. |
| 6,162,184 A | 12/2000 | Swanson et al. |
| 6,165,163 A | 12/2000 | Chien et al. |
| 6,165,172 A | 12/2000 | Farley et al. |
| 6,165,187 A | 12/2000 | Reger et al. |
| 6,168,594 B1 | 1/2001 | Lafontaine et al. |
| 6,171,321 B1 | 1/2001 | Gifford, III et al. |
| 6,179,832 B1 | 1/2001 | Jones et al. |
| 6,179,835 B1 | 1/2001 | Panescu et al. |
| 6,179,859 B1 | 1/2001 | Bates et al. |
| 6,183,468 B1 | 2/2001 | Swanson et al. |
| 6,183,486 B1 | 2/2001 | Snow et al. |
| 6,190,379 B1 | 2/2001 | Heuser et al. |
| 6,191,862 B1 | 2/2001 | Swanson et al. |
| 6,197,021 B1 | 3/2001 | Panescu et al. |
| 6,200,266 B1 | 3/2001 | Shokrollahi et al. |
| 6,203,537 B1 | 3/2001 | Adrian |
| 6,203,561 B1 | 3/2001 | Ramee et al. |
| 6,210,406 B1 | 4/2001 | Webster |
| 6,211,247 B1 | 4/2001 | Goodman |
| 6,216,704 B1 | 4/2001 | Ingle et al. |
| 6,217,576 B1 | 4/2001 | Tu et al. |
| 6,219,577 B1 | 4/2001 | Brown, III et al. |
| 6,228,076 B1 | 5/2001 | Winston et al. |
| 6,228,109 B1 | 5/2001 | Tu et al. |
| 6,231,516 B1 | 5/2001 | Keilman et al. |
| 6,231,587 B1 | 5/2001 | Makower |
| 6,235,044 B1 | 5/2001 | Root et al. |
| 6,236,883 B1 | 5/2001 | Ciaccio et al. |
| 6,237,605 B1 | 5/2001 | Vaska et al. |
| 6,238,389 B1 | 5/2001 | Paddock et al. |
| 6,238,392 B1 | 5/2001 | Long |
| 6,241,666 B1 | 6/2001 | Pomeranz et al. |
| 6,241,753 B1 | 6/2001 | Knowlton |
| 6,245,020 B1 | 6/2001 | Moore et al. |
| 6,245,045 B1 | 6/2001 | Stratienko |
| 6,248,126 B1 | 6/2001 | Lesser et al. |
| 6,251,128 B1 | 6/2001 | Knopp et al. |
| 6,258,087 B1 | 7/2001 | Edwards et al. |
| 6,273,886 B1 | 8/2001 | Edwards et al. |
| 6,280,466 B1 | 8/2001 | Kugler et al. |
| 6,283,935 B1 | 9/2001 | Laufer et al. |
| 6,283,959 B1 | 9/2001 | Lalonde et al. |
| 6,284,743 B1 | 9/2001 | Parmacek et al. |
| 6,287,323 B1 | 9/2001 | Hammerslag |
| 6,290,696 B1 | 9/2001 | Lafontaine |
| 6,292,695 B1 | 9/2001 | Webster, Jr. et al. |
| 6,293,942 B1 | 9/2001 | Goble et al. |
| 6,293,943 B1 | 9/2001 | Panescu et al. |
| 6,296,619 B1 | 10/2001 | Brisken et al. |
| 6,298,256 B1 | 10/2001 | Meyer |
| 6,299,379 B1 | 10/2001 | Lewis |
| 6,299,623 B1 | 10/2001 | Wulfman |
| 6,309,379 B1 | 10/2001 | Willard et al. |
| 6,309,399 B1 | 10/2001 | Barbut et al. |
| 6,311,090 B1 | 10/2001 | Knowlton |
| 6,317,615 B1 | 11/2001 | KenKnight et al. |
| 6,319,242 B1 | 11/2001 | Patterson et al. |
| 6,319,251 B1 | 11/2001 | Tu et al. |
| 6,322,559 B1 | 11/2001 | Daulton et al. |
| 6,325,797 B1 | 12/2001 | Stewart et al. |
| 6,325,799 B1 | 12/2001 | Goble |
| 6,328,699 B1 | 12/2001 | Eigler et al. |
| 6,346,074 B1 | 2/2002 | Roth |
| 6,346,104 B2 | 2/2002 | Daly et al. |
| 6,350,248 B1 | 2/2002 | Knudson et al. |
| 6,350,276 B1 | 2/2002 | Knowlton |
| 6,353,751 B1 | 3/2002 | Swanson et al. |
| 6,355,029 B1 | 3/2002 | Joye et al. |
| 6,357,447 B1 | 3/2002 | Swanson et al. |
| 6,361,519 B1 | 3/2002 | Knudson et al. |
| 6,364,840 B1 | 4/2002 | Crowley |
| 6,371,965 B2 | 4/2002 | Gifford, III et al. |
| 6,375,668 B1 | 4/2002 | Gifford et al. |
| 6,377,854 B1 | 4/2002 | Knowlton |
| 6,377,855 B1 | 4/2002 | Knowlton |
| 6,379,352 B1 | 4/2002 | Reynolds et al. |
| 6,379,373 B1 | 4/2002 | Sawhney et al. |
| 6,381,497 B1 | 4/2002 | Knowlton |
| 6,381,498 B1 | 4/2002 | Knowlton |
| 6,383,151 B1 | 5/2002 | Diederich et al. |
| 6,387,105 B1 | 5/2002 | Gifford, III et al. |
| 6,387,380 B1 | 5/2002 | Knowlton |
| 6,389,311 B1 | 5/2002 | Whayne et al. |
| 6,389,314 B2 | 5/2002 | Feiring |
| 6,391,024 B1 | 5/2002 | Sun et al. |
| 6,394,096 B1 | 5/2002 | Constantz |
| 6,394,956 B1 | 5/2002 | Chandrasekaran et al. |
| 6,398,780 B1 | 6/2002 | Farley et al. |
| 6,398,782 B1 | 6/2002 | Pecor et al. |
| 6,398,792 B1 | 6/2002 | O'Connor |
| 6,401,720 B1 | 6/2002 | Stevens et al. |
| 6,402,719 B1 | 6/2002 | Ponzi et al. |
| 6,405,090 B1 | 6/2002 | Knowlton |
| 6,409,723 B1 | 6/2002 | Edwards |
| 6,413,255 B1 | 7/2002 | Stern |
| 6,421,559 B1 | 7/2002 | Pearlman |
| 6,423,057 B1 | 7/2002 | He et al. |
| 6,425,867 B1 | 7/2002 | Vaezy et al. |
| 6,425,912 B1 | 7/2002 | Knowlton |
| 6,427,118 B1 | 7/2002 | Suzuki |

(56) References Cited

U.S. PATENT DOCUMENTS

| | | |
|---|---|---|
| 6,428,534 B1 | 8/2002 | Joye et al. |
| 6,428,536 B2 | 8/2002 | Panescu et al. |
| 6,430,446 B1 | 8/2002 | Knowlton |
| 6,432,102 B2 | 8/2002 | Joye et al. |
| 6,436,056 B1 | 8/2002 | Wang et al. |
| 6,438,424 B1 | 8/2002 | Knowlton |
| 6,440,125 B1 | 8/2002 | Rentrop |
| 6,442,413 B1 | 8/2002 | Silver |
| 6,443,965 B1 | 9/2002 | Gifford, III et al. |
| 6,445,939 B1 | 9/2002 | Swanson et al. |
| 6,447,505 B2 | 9/2002 | McGovern et al. |
| 6,447,509 B1 | 9/2002 | Bonnet et al. |
| 6,451,034 B1 | 9/2002 | Gifford, III et al. |
| 6,451,044 B1 | 9/2002 | Naghavi et al. |
| 6,453,202 B1 | 9/2002 | Knowlton |
| 6,454,737 B1 | 9/2002 | Nita et al. |
| 6,454,757 B1 | 9/2002 | Nita et al. |
| 6,454,775 B1 | 9/2002 | Demarais et al. |
| 6,458,098 B1 | 10/2002 | Kanesaka |
| 6,461,378 B1 | 10/2002 | Knowlton |
| 6,468,276 B1 | 10/2002 | McKay |
| 6,468,297 B1 | 10/2002 | Williams et al. |
| 6,470,216 B1 | 10/2002 | Knowlton |
| 6,470,219 B1 | 10/2002 | Edwards et al. |
| 6,471,689 B1 * | 10/2002 | Joseph et al. ............. 604/892.1 |
| 6,471,696 B1 | 10/2002 | Berube et al. |
| 6,475,213 B1 | 11/2002 | Whayne et al. |
| 6,475,215 B1 | 11/2002 | Tanrisever |
| 6,475,238 B1 | 11/2002 | Fedida et al. |
| 6,477,426 B1 | 11/2002 | Fenn et al. |
| 6,480,745 B2 | 11/2002 | Nelson et al. |
| 6,481,704 B1 | 11/2002 | Koster et al. |
| 6,482,202 B1 | 11/2002 | Goble et al. |
| 6,484,052 B1 | 11/2002 | Visuri et al. |
| 6,485,489 B2 | 11/2002 | Teirstein et al. |
| 6,488,679 B1 | 12/2002 | Swanson et al. |
| 6,489,307 B1 | 12/2002 | Phillips et al. |
| 6,491,705 B2 | 12/2002 | Gifford, III et al. |
| 6,494,891 B1 | 12/2002 | Cornish et al. |
| 6,497,711 B1 | 12/2002 | Plaia et al. |
| 6,500,172 B1 | 12/2002 | Panescu et al. |
| 6,500,174 B1 | 12/2002 | Maguire et al. |
| 6,508,765 B2 | 1/2003 | Suorsa et al. |
| 6,508,804 B2 | 1/2003 | Sarge et al. |
| 6,508,815 B1 | 1/2003 | Strul et al. |
| 6,511,478 B1 | 1/2003 | Burnside et al. |
| 6,511,496 B1 | 1/2003 | Huter et al. |
| 6,511,500 B1 | 1/2003 | Rahme |
| 6,514,236 B1 | 2/2003 | Stratienko |
| 6,514,245 B1 | 2/2003 | Williams et al. |
| 6,514,248 B1 | 2/2003 | Eggers et al. |
| 6,517,534 B1 | 2/2003 | McGovern et al. |
| 6,517,572 B2 | 2/2003 | Kugler et al. |
| 6,522,913 B2 | 2/2003 | Swanson et al. |
| 6,522,926 B1 | 2/2003 | Kieval et al. |
| 6,524,299 B1 | 2/2003 | Tran et al. |
| 6,527,765 B2 | 3/2003 | Kelman et al. |
| 6,527,769 B2 | 3/2003 | Langberg et al. |
| 6,540,761 B2 | 4/2003 | Houser |
| 6,542,781 B1 | 4/2003 | Koblish et al. |
| 6,544,780 B1 | 4/2003 | Wang |
| 6,546,272 B1 | 4/2003 | MacKinnon et al. |
| 6,547,788 B1 | 4/2003 | Maguire et al. |
| 6,549,800 B1 | 4/2003 | Atalar et al. |
| 6,552,796 B2 | 4/2003 | Magnin et al. |
| 6,554,780 B1 | 4/2003 | Sampson et al. |
| 6,558,381 B2 | 5/2003 | Ingle et al. |
| 6,558,382 B2 | 5/2003 | Jahns et al. |
| 6,564,096 B2 | 5/2003 | Mest |
| 6,565,582 B2 | 5/2003 | Gifford, III et al. |
| 6,569,109 B2 | 5/2003 | Sakurai et al. |
| 6,569,177 B1 | 5/2003 | Dillard et al. |
| 6,570,659 B2 | 5/2003 | Schmitt |
| 6,572,551 B1 | 6/2003 | Smith et al. |
| 6,572,612 B2 | 6/2003 | Stewart et al. |
| 6,577,902 B1 | 6/2003 | Laufer et al. |
| 6,579,308 B1 | 6/2003 | Jansen et al. |
| 6,579,311 B1 | 6/2003 | Makower |
| 6,582,423 B1 | 6/2003 | Thapliyal et al. |
| 6,589,238 B2 | 7/2003 | Edwards et al. |
| 6,592,526 B1 | 7/2003 | Lenker |
| 6,592,567 B1 | 7/2003 | Levin et al. |
| 6,595,959 B1 | 7/2003 | Stratienko |
| 6,600,956 B2 | 7/2003 | Maschino et al. |
| 6,602,242 B1 | 8/2003 | Fung et al. |
| 6,602,246 B1 | 8/2003 | Joye et al. |
| 6,605,061 B2 | 8/2003 | Vantassel et al. |
| 6,605,084 B2 | 8/2003 | Acker et al. |
| 6,623,452 B2 | 9/2003 | Chien et al. |
| 6,623,453 B1 | 9/2003 | Guibert et al. |
| 6,632,193 B1 | 10/2003 | Davison et al. |
| 6,632,196 B1 | 10/2003 | Houser |
| 6,645,223 B2 | 11/2003 | Boyle et al. |
| 6,648,854 B1 | 11/2003 | Patterson et al. |
| 6,648,878 B2 | 11/2003 | Lafontaine |
| 6,648,879 B2 | 11/2003 | Joye et al. |
| 6,651,672 B2 | 11/2003 | Roth |
| 6,652,513 B2 | 11/2003 | Panescu et al. |
| 6,652,515 B1 | 11/2003 | Maguire et al. |
| 6,656,136 B1 | 12/2003 | Weng et al. |
| 6,658,279 B2 | 12/2003 | Swanson et al. |
| 6,659,981 B2 | 12/2003 | Stewart et al. |
| 6,666,858 B2 | 12/2003 | Lafontaine |
| 6,666,863 B2 | 12/2003 | Wentzel et al. |
| 6,669,655 B1 | 12/2003 | Acker et al. |
| 6,669,692 B1 | 12/2003 | Nelson et al. |
| 6,673,040 B1 | 1/2004 | Samson et al. |
| 6,673,064 B1 | 1/2004 | Rentrop |
| 6,673,066 B2 | 1/2004 | Werneth |
| 6,673,090 B2 | 1/2004 | Root et al. |
| 6,673,101 B1 | 1/2004 | Fitzgerald et al. |
| 6,673,290 B1 | 1/2004 | Whayne et al. |
| 6,676,678 B2 | 1/2004 | Gifford, III et al. |
| 6,679,268 B2 | 1/2004 | Stevens et al. |
| 6,681,773 B2 | 1/2004 | Murphy et al. |
| 6,682,541 B1 | 1/2004 | Gifford, III et al. |
| 6,684,098 B2 | 1/2004 | Oshio et al. |
| 6,685,732 B2 | 2/2004 | Kramer |
| 6,685,733 B1 | 2/2004 | Dae et al. |
| 6,689,086 B1 | 2/2004 | Nita et al. |
| 6,689,148 B2 | 2/2004 | Sawhney et al. |
| 6,690,181 B1 | 2/2004 | Dowdeswell et al. |
| 6,692,490 B1 | 2/2004 | Edwards |
| 6,695,830 B2 | 2/2004 | Vigil et al. |
| 6,695,857 B2 | 2/2004 | Gifford, III et al. |
| 6,699,241 B2 | 3/2004 | Rappaport et al. |
| 6,699,257 B2 | 3/2004 | Gifford, III et al. |
| 6,702,748 B1 | 3/2004 | Nita et al. |
| 6,702,811 B2 | 3/2004 | Stewart et al. |
| 6,706,010 B1 | 3/2004 | Miki et al. |
| 6,706,011 B1 | 3/2004 | Murphy-Chutorian et al. |
| 6,706,037 B2 | 3/2004 | Zvuloni et al. |
| 6,709,431 B2 | 3/2004 | Lafontaine |
| 6,711,429 B1 | 3/2004 | Gilboa et al. |
| 6,712,815 B2 | 3/2004 | Sampson et al. |
| 6,714,822 B2 | 3/2004 | King et al. |
| 6,716,184 B2 | 4/2004 | Vaezy et al. |
| 6,720,350 B2 | 4/2004 | Kunz et al. |
| 6,723,043 B2 | 4/2004 | Kleeman et al. |
| 6,723,064 B2 | 4/2004 | Babaev |
| 6,736,811 B2 | 5/2004 | Panescu et al. |
| 6,743,184 B2 | 6/2004 | Sampson et al. |
| 6,746,401 B2 | 6/2004 | Panescu |
| 6,746,464 B1 | 6/2004 | Makower |
| 6,746,474 B2 | 6/2004 | Saadat |
| 6,748,953 B2 | 6/2004 | Sherry et al. |
| 6,749,607 B2 | 6/2004 | Edwards et al. |
| 6,752,805 B2 | 6/2004 | Maguire et al. |
| 6,760,616 B2 | 7/2004 | Hoey et al. |
| 6,763,261 B2 | 7/2004 | Casscells, III et al. |
| 6,764,501 B2 | 7/2004 | Ganz |
| 6,769,433 B2 | 8/2004 | Zikorus et al. |
| 6,770,070 B1 | 8/2004 | Balbierz |
| 6,771,996 B2 | 8/2004 | Bowe et al. |

(56) References Cited

U.S. PATENT DOCUMENTS

| | | | |
|---|---|---|---|
| 6,773,433 B2 | 8/2004 | Stewart et al. |
| 6,786,900 B2 | 9/2004 | Joye et al. |
| 6,786,901 B2 | 9/2004 | Joye et al. |
| 6,786,904 B2 | 9/2004 | Doscher et al. |
| 6,788,977 B2 | 9/2004 | Fenn et al. |
| 6,790,206 B2 | 9/2004 | Panescu |
| 6,790,222 B2 | 9/2004 | Kugler et al. |
| 6,796,981 B2 | 9/2004 | Wham et al. |
| 6,797,933 B1 | 9/2004 | Mendis et al. |
| 6,797,960 B1 | 9/2004 | Spartiotis et al. |
| 6,800,075 B2 | 10/2004 | Mische et al. |
| 6,802,857 B1 | 10/2004 | Walsh et al. |
| 6,807,444 B2 | 10/2004 | Tu et al. |
| 6,811,550 B2 | 11/2004 | Holland et al. |
| 6,813,520 B2 | 11/2004 | Truckai et al. |
| 6,814,730 B2 | 11/2004 | Li |
| 6,814,733 B2 | 11/2004 | Schwartz et al. |
| 6,823,205 B1 | 11/2004 | Jara |
| 6,824,516 B2 | 11/2004 | Batten et al. |
| 6,827,726 B2 | 12/2004 | Parodi |
| 6,827,926 B2 | 12/2004 | Robinson et al. |
| 6,829,497 B2 | 12/2004 | Mogul |
| 6,830,568 B1 | 12/2004 | Kesten et al. |
| 6,837,886 B2 | 1/2005 | Collins et al. |
| 6,837,888 B2 | 1/2005 | Ciarrocca et al. |
| 6,845,267 B2 | 1/2005 | Harrison et al. |
| 6,847,848 B2 | 1/2005 | Sterzer |
| 6,849,073 B2 | 2/2005 | Hoey et al. |
| 6,849,075 B2 | 2/2005 | Bertolero et al. |
| 6,853,425 B2 | 2/2005 | Kim et al. |
| 6,855,123 B2 | 2/2005 | Nita |
| 6,855,143 B2 | 2/2005 | Davison et al. |
| 6,869,431 B2 | 3/2005 | Maguire et al. |
| 6,872,183 B2 | 3/2005 | Sampson et al. |
| 6,884,260 B2 | 4/2005 | Kugler et al. |
| 6,889,694 B2 | 5/2005 | Hooven |
| 6,893,436 B2 | 5/2005 | Woodard et al. |
| 6,895,077 B2 | 5/2005 | Karellas et al. |
| 6,895,265 B2 | 5/2005 | Silver |
| 6,898,454 B2 | 5/2005 | Atalar et al. |
| 6,899,711 B2 | 5/2005 | Stewart et al. |
| 6,899,718 B2 | 5/2005 | Gifford, III et al. |
| 6,905,494 B2 | 6/2005 | Yon et al. |
| 6,908,462 B2 | 6/2005 | Joye et al. |
| 6,909,009 B2 | 6/2005 | Koridze |
| 6,911,026 B1 | 6/2005 | Hall et al. |
| 6,915,806 B2 | 7/2005 | Pacek et al. |
| 6,923,805 B1 | 8/2005 | LaFontaine et al. |
| 6,926,246 B2 | 8/2005 | Ginggen |
| 6,926,713 B2 | 8/2005 | Rioux et al. |
| 6,926,716 B2 | 8/2005 | Baker et al. |
| 6,929,009 B2 | 8/2005 | Makower et al. |
| 6,929,632 B2 | 8/2005 | Nita et al. |
| 6,929,639 B2 | 8/2005 | Lafontaine |
| 6,932,776 B2 | 8/2005 | Carr |
| 6,936,047 B2 | 8/2005 | Nasab et al. |
| 6,942,620 B2 | 9/2005 | Nita et al. |
| 6,942,657 B2 | 9/2005 | Sinofsky et al. |
| 6,942,677 B2 | 9/2005 | Nita et al. |
| 6,942,692 B2 | 9/2005 | Landau et al. |
| 6,949,097 B2 | 9/2005 | Stewart et al. |
| 6,949,121 B1 | 9/2005 | Laguna |
| 6,952,615 B2 | 10/2005 | Satake |
| 6,953,425 B2 | 10/2005 | Brister |
| 6,955,174 B2 | 10/2005 | Joye |
| 6,955,175 B2 | 10/2005 | Stevens et al. |
| 6,958,075 B2 | 10/2005 | Mon et al. |
| 6,959,711 B2 | 11/2005 | Murphy et al. |
| 6,960,207 B2 | 11/2005 | Vanney et al. |
| 6,962,584 B1 | 11/2005 | Stone |
| 6,964,660 B2 | 11/2005 | Maguire et al. |
| 6,966,908 B2 | 11/2005 | Maguire et al. |
| 6,972,015 B2 | 12/2005 | Joye et al. |
| 6,972,024 B1 | 12/2005 | Kilpatrick |
| 6,974,456 B2 | 12/2005 | Edwards et al. |
| 6,978,174 B2 | 12/2005 | Gelfand et al. |
| 6,979,329 B2 | 12/2005 | Burnside et al. |
| 6,979,420 B2 | 12/2005 | Weber |
| 6,984,238 B2 | 1/2006 | Gifford, III et al. |
| 6,985,774 B2 | 1/2006 | Kieval et al. |
| 6,986,739 B2 | 1/2006 | Warren et al. |
| 6,989,009 B2 | 1/2006 | Lafontaine |
| 6,989,010 B2 | 1/2006 | Francischelli et al. |
| 6,991,617 B2 | 1/2006 | Hektner et al. |
| 7,001,378 B2 | 2/2006 | Yon et al. |
| 7,006,858 B2 | 2/2006 | Silver et al. |
| 7,008,667 B2 | 3/2006 | Chudzik et al. |
| 7,011,508 B2 | 3/2006 | Lum |
| 7,022,105 B1 | 4/2006 | Edwards |
| 7,022,120 B2 | 4/2006 | Lafontaine |
| 7,025,767 B2 | 4/2006 | Schaefer et al. |
| 7,033,322 B2 | 4/2006 | Silver |
| 7,033,372 B1 | 4/2006 | Cahalan |
| 7,041,098 B2 | 5/2006 | Farley et al. |
| 7,050,848 B2 | 5/2006 | Hoey et al. |
| 7,063,670 B2 | 6/2006 | Sampson et al. |
| 7,063,679 B2 | 6/2006 | Maguire et al. |
| 7,063,719 B2 | 6/2006 | Jansen et al. |
| 7,066,895 B2 | 6/2006 | Podany |
| 7,066,900 B2 | 6/2006 | Botto et al. |
| 7,066,904 B2 * | 6/2006 | Rosenthal et al. ........ 604/103.08 |
| 7,072,720 B2 | 7/2006 | Puskas |
| 7,074,217 B2 | 7/2006 | Strul et al. |
| 7,081,112 B2 | 7/2006 | Joye et al. |
| 7,081,114 B2 | 7/2006 | Rashidi |
| 7,083,614 B2 | 8/2006 | Fjield et al. |
| 7,084,276 B2 | 8/2006 | Vu et al. |
| 7,087,026 B2 | 8/2006 | Callister et al. |
| 7,087,051 B2 | 8/2006 | Bourne et al. |
| 7,087,052 B2 | 8/2006 | Sampson et al. |
| 7,087,053 B2 | 8/2006 | Vanney |
| 7,089,065 B2 | 8/2006 | Westlund et al. |
| 7,090,655 B2 | 8/2006 | Barry |
| 7,097,641 B1 | 8/2006 | Arless et al. |
| 7,100,614 B2 | 9/2006 | Stevens et al. |
| 7,101,368 B2 | 9/2006 | Lafontaine |
| 7,104,983 B2 | 9/2006 | Grasso, III et al. |
| 7,104,987 B2 | 9/2006 | Biggs et al. |
| 7,108,715 B2 | 9/2006 | Lawrence-Brown et al. |
| 7,112,196 B2 | 9/2006 | Brosch et al. |
| 7,112,198 B2 | 9/2006 | Satake |
| 7,112,211 B2 | 9/2006 | Gifford, III et al. |
| 7,122,019 B1 | 10/2006 | Kesten et al. |
| 7,122,033 B2 | 10/2006 | Wood |
| 7,134,438 B2 | 11/2006 | Makower et al. |
| 7,137,963 B2 | 11/2006 | Nita et al. |
| 7,137,980 B2 | 11/2006 | Buysse et al. |
| 7,153,315 B2 | 12/2006 | Miller |
| 7,155,271 B2 | 12/2006 | Halperin et al. |
| 7,157,491 B2 | 1/2007 | Mewshaw et al. |
| 7,157,492 B2 | 1/2007 | Mewshaw et al. |
| 7,158,832 B2 | 1/2007 | Kieval et al. |
| 7,160,296 B2 | 1/2007 | Pearson et al. |
| 7,162,303 B2 | 1/2007 | Levin et al. |
| 7,165,551 B2 | 1/2007 | Edwards et al. |
| 7,169,144 B2 | 1/2007 | Hoey et al. |
| 7,172,589 B2 | 2/2007 | Lafontaine |
| 7,172,610 B2 | 2/2007 | Heitzmann et al. |
| 7,181,261 B2 | 2/2007 | Silver et al. |
| 7,184,811 B2 | 2/2007 | Phan et al. |
| 7,184,827 B1 | 2/2007 | Edwards |
| 7,189,227 B2 | 3/2007 | Lafontaine |
| 7,192,427 B2 | 3/2007 | Chapelon et al. |
| 7,192,586 B2 | 3/2007 | Bander |
| 7,197,354 B2 | 3/2007 | Sobe |
| 7,198,632 B2 | 4/2007 | Lim et al. |
| 7,200,445 B1 | 4/2007 | Dalbec et al. |
| 7,201,749 B2 | 4/2007 | Govari et al. |
| 7,203,537 B2 | 4/2007 | Mower |
| 7,214,234 B2 | 5/2007 | Rapacki et al. |
| 7,220,233 B2 | 5/2007 | Nita et al. |
| 7,220,239 B2 | 5/2007 | Wilson et al. |
| 7,220,257 B1 | 5/2007 | Lafontaine |
| 7,220,270 B2 | 5/2007 | Sawhney et al. |

(56) References Cited

U.S. PATENT DOCUMENTS

| | | |
|---|---|---|
| 7,232,458 B2 | 6/2007 | Saadat |
| 7,232,459 B2 | 6/2007 | Greenberg et al. |
| 7,238,184 B2 | 7/2007 | Megerman et al. |
| 7,241,273 B2 | 7/2007 | Maguire et al. |
| 7,241,736 B2 | 7/2007 | Hunter et al. |
| 7,247,141 B2 | 7/2007 | Makin et al. |
| 7,250,041 B2 | 7/2007 | Chiu et al. |
| 7,250,440 B2 | 7/2007 | Mewshaw et al. |
| 7,252,664 B2 | 8/2007 | Nasab et al. |
| 7,252,679 B2 | 8/2007 | Fischell et al. |
| 7,264,619 B2 | 9/2007 | Venturelli |
| 7,279,600 B2 | 10/2007 | Mewshaw et al. |
| 7,280,863 B2 | 10/2007 | Shachar |
| 7,282,213 B2 | 10/2007 | Schroeder et al. |
| 7,285,119 B2 | 10/2007 | Stewart et al. |
| 7,285,120 B2 | 10/2007 | Im et al. |
| 7,288,089 B2 | 10/2007 | Yon et al. |
| 7,288,096 B2 | 10/2007 | Chin |
| 7,291,146 B2 | 11/2007 | Steinke et al. |
| 7,293,562 B2 | 11/2007 | Malecki et al. |
| 7,294,125 B2 | 11/2007 | Phalen et al. |
| 7,294,126 B2 | 11/2007 | Sampson et al. |
| 7,294,127 B2 | 11/2007 | Leung et al. |
| 7,297,131 B2 | 11/2007 | Nita |
| 7,297,475 B2 | 11/2007 | Koiwai et al. |
| 7,300,433 B2 | 11/2007 | Lane et al. |
| 7,301,108 B2 | 11/2007 | Egitto et al. |
| 7,310,150 B2 | 12/2007 | Guillermo et al. |
| 7,313,430 B2 | 12/2007 | Urquhart et al. |
| 7,314,483 B2 | 1/2008 | Landau et al. |
| 7,317,077 B2 | 1/2008 | Averback et al. |
| 7,323,006 B2 | 1/2008 | Andreas et al. |
| 7,326,206 B2 | 2/2008 | Paul et al. |
| 7,326,226 B2 | 2/2008 | Root et al. |
| 7,326,235 B2 | 2/2008 | Edwards |
| 7,326,237 B2 | 2/2008 | DePalma et al. |
| 7,329,236 B2 | 2/2008 | Kesten et al. |
| 7,335,180 B2 | 2/2008 | Nita et al. |
| 7,335,192 B2 | 2/2008 | Keren et al. |
| 7,338,467 B2 | 3/2008 | Lutter |
| 7,341,570 B2 | 3/2008 | Keren et al. |
| 7,343,195 B2 | 3/2008 | Strommer et al. |
| 7,347,857 B2 | 3/2008 | Anderson et al. |
| 7,348,003 B2 | 3/2008 | Salcedo et al. |
| 7,352,593 B2 | 4/2008 | Zeng et al. |
| 7,354,927 B2 | 4/2008 | Vu |
| 7,359,732 B2 | 4/2008 | Kim et al. |
| 7,361,341 B2 | 4/2008 | Salcedo et al. |
| 7,364,566 B2 | 4/2008 | Elkins et al. |
| 7,367,970 B2 | 5/2008 | Govari et al. |
| 7,367,975 B2 | 5/2008 | Malecki et al. |
| 7,371,231 B2 | 5/2008 | Rioux et al. |
| 7,387,126 B2 | 6/2008 | Cox et al. |
| 7,393,338 B2 | 7/2008 | Nita |
| 7,396,355 B2 | 7/2008 | Goldman et al. |
| 7,402,151 B2 | 7/2008 | Rosenman et al. |
| 7,402,312 B2 | 7/2008 | Rosen et al. |
| 7,404,824 B1 | 7/2008 | Webler et al. |
| 7,406,970 B2 | 8/2008 | Zikorus et al. |
| 7,407,502 B2 | 8/2008 | Strul et al. |
| 7,407,506 B2 | 8/2008 | Makower |
| 7,407,671 B2 | 8/2008 | McBride et al. |
| 7,408,021 B2 | 8/2008 | Averback et al. |
| 7,410,486 B2 | 8/2008 | Fuimaono et al. |
| 7,413,556 B2 | 8/2008 | Zhang et al. |
| 7,425,212 B1 | 9/2008 | Danek et al. |
| 7,426,409 B2 | 9/2008 | Casscells, III et al. |
| 7,435,248 B2 | 10/2008 | Taimisto et al. |
| 7,447,453 B2 | 11/2008 | Kim et al. |
| 7,447,543 B2 | 11/2008 | Belacazar et al. |
| 7,449,018 B2 | 11/2008 | Kramer |
| 7,452,538 B2 | 11/2008 | Ni et al. |
| 7,473,890 B2 | 1/2009 | Grier et al. |
| 7,476,384 B2 | 1/2009 | Ni et al. |
| 7,479,157 B2 | 1/2009 | Weber et al. |
| 7,481,803 B2 | 1/2009 | Kesten et al. |
| 7,485,104 B2 | 2/2009 | Kieval |
| 7,486,805 B2 | 2/2009 | Krattiger |
| 7,487,780 B2 | 2/2009 | Hooven |
| 7,493,154 B2 | 2/2009 | Bonner et al. |
| 7,494,485 B2 | 2/2009 | Beck et al. |
| 7,494,486 B2 | 2/2009 | Mische et al. |
| 7,494,488 B2 | 2/2009 | Weber |
| 7,494,661 B2 | 2/2009 | Sanders |
| 7,495,439 B2 | 2/2009 | Wiggins |
| 7,497,858 B2 | 3/2009 | Chapelon et al. |
| 7,499,745 B2 | 3/2009 | Littrup et al. |
| 7,500,985 B2 | 3/2009 | Saadat |
| 7,505,812 B1 | 3/2009 | Eggers et al. |
| 7,505,816 B2 | 3/2009 | Schmeling et al. |
| 7,507,233 B2 | 3/2009 | Littrup et al. |
| 7,507,235 B2 | 3/2009 | Keogh et al. |
| 7,511,494 B2 | 3/2009 | Wedeen |
| 7,512,445 B2 | 3/2009 | Truckai et al. |
| 7,527,643 B2 | 5/2009 | Case et al. |
| 7,529,589 B2 | 5/2009 | Williams et al. |
| 7,540,852 B2 | 6/2009 | Nita et al. |
| 7,540,870 B2 | 6/2009 | Babaev |
| RE40,863 E | 7/2009 | Tay et al. |
| 7,556,624 B2 | 7/2009 | Laufer et al. |
| 7,558,625 B2 | 7/2009 | Levin et al. |
| 7,563,247 B2 | 7/2009 | Maguire et al. |
| 7,563,262 B2 | 7/2009 | Winston et al. |
| 7,566,319 B2 | 7/2009 | McAuley et al. |
| 7,569,052 B2 | 8/2009 | Phan et al. |
| 7,582,111 B2 | 9/2009 | Krolik et al. |
| 7,584,004 B2 | 9/2009 | Caparso et al. |
| 7,585,835 B2 | 9/2009 | Hill et al. |
| 7,591,996 B2 | 9/2009 | Hwang et al. |
| 7,597,704 B2 | 10/2009 | Frazier et al. |
| 7,598,228 B2 | 10/2009 | Hattori et al. |
| 7,599,730 B2 | 10/2009 | Hunter et al. |
| 7,603,166 B2 | 10/2009 | Casscells, III et al. |
| 7,604,608 B2 | 10/2009 | Nita et al. |
| 7,604,633 B2 | 10/2009 | Truckai et al. |
| 7,615,015 B2 | 11/2009 | Coleman |
| 7,615,072 B2 | 11/2009 | Rust et al. |
| 7,617,005 B2 | 11/2009 | Demarais et al. |
| 7,620,451 B2 | 11/2009 | Demarais et al. |
| 7,621,902 B2 | 11/2009 | Nita et al. |
| 7,621,929 B2 | 11/2009 | Nita et al. |
| 7,626,015 B2 | 12/2009 | Feinstein et al. |
| 7,626,235 B2 | 12/2009 | Kinoshita |
| 7,632,268 B2 | 12/2009 | Edwards et al. |
| 7,632,845 B2 | 12/2009 | Vu et al. |
| 7,635,383 B2 | 12/2009 | Gumm |
| 7,640,046 B2 | 12/2009 | Pastore et al. |
| 7,641,633 B2 | 1/2010 | Laufer et al. |
| 7,641,679 B2 | 1/2010 | Joye et al. |
| 7,646,544 B2 | 1/2010 | Batchko et al. |
| 7,647,115 B2 | 1/2010 | Levin et al. |
| 7,653,438 B2 | 1/2010 | Deem et al. |
| 7,655,006 B2 | 2/2010 | Sauvageau et al. |
| 7,662,114 B2 | 2/2010 | Seip et al. |
| 7,664,548 B2 | 2/2010 | Amurthur et al. |
| 7,670,279 B2 | 3/2010 | Gertner |
| 7,670,335 B2 | 3/2010 | Keidar |
| 7,671,084 B2 | 3/2010 | Mewshaw et al. |
| 7,678,104 B2 | 3/2010 | Keidar |
| 7,678,106 B2 | 3/2010 | Lee |
| 7,678,108 B2 | 3/2010 | Chrisitian et al. |
| 7,691,080 B2 | 4/2010 | Seward et al. |
| 7,699,809 B2 | 4/2010 | Urmey |
| 7,706,882 B2 | 4/2010 | Francischelli et al. |
| 7,715,912 B2 | 5/2010 | Rezai et al. |
| 7,717,853 B2 | 5/2010 | Nita |
| 7,717,909 B2 | 5/2010 | Strul et al. |
| 7,717,948 B2 | 5/2010 | Demarais et al. |
| 7,722,539 B2 | 5/2010 | Carter et al. |
| 7,725,157 B2 | 5/2010 | Dumoulin et al. |
| 7,727,178 B2 | 6/2010 | Wilson et al. |
| 7,736,317 B2 | 6/2010 | Stephens et al. |
| 7,736,360 B2 | 6/2010 | Mody et al. |
| 7,736,362 B2 | 6/2010 | Eberl et al. |

(56) References Cited

U.S. PATENT DOCUMENTS

| | | | |
|---|---|---|---|
| 7,738,952 | B2 | 6/2010 | Yun et al. |
| 7,740,629 | B2 | 6/2010 | Anderson et al. |
| 7,741,299 | B2 | 6/2010 | Feinstein et al. |
| 7,742,795 | B2 | 6/2010 | Stone et al. |
| 7,744,594 | B2 | 6/2010 | Yamazaki et al. |
| 7,753,907 | B2 | 7/2010 | DiMatteo et al. |
| 7,756,583 | B2 | 7/2010 | Demarais et al. |
| 7,758,510 | B2 | 7/2010 | Nita et al. |
| 7,758,520 | B2 | 7/2010 | Griffin et al. |
| 7,759,315 | B2 | 7/2010 | Cuzzocrea et al. |
| 7,766,833 | B2 | 8/2010 | Lee et al. |
| 7,766,878 | B2 | 8/2010 | Tremaglio, Jr. et al. |
| 7,766,892 | B2 | 8/2010 | Keren et al. |
| 7,767,844 | B2 | 8/2010 | Lee et al. |
| 7,769,427 | B2 | 8/2010 | Shachar |
| 7,771,372 | B2 | 8/2010 | Wilson |
| 7,771,421 | B2 | 8/2010 | Stewart et al. |
| 7,776,967 | B2 | 8/2010 | Perry et al. |
| 7,777,486 | B2 | 8/2010 | Hargreaves et al. |
| 7,780,660 | B2 | 8/2010 | Bourne et al. |
| 7,789,876 | B2 | 9/2010 | Zikorus et al. |
| 7,792,568 | B2 | 9/2010 | Zhong et al. |
| 7,799,021 | B2 | 9/2010 | Leung et al. |
| 7,803,168 | B2 | 9/2010 | Gifford et al. |
| 7,806,871 | B2 | 10/2010 | Li et al. |
| 7,811,265 | B2 | 10/2010 | Hering et al. |
| 7,811,281 | B1 | 10/2010 | Rentrop |
| 7,811,313 | B2 | 10/2010 | Mon et al. |
| 7,816,511 | B2 | 10/2010 | Kawashima et al. |
| 7,818,053 | B2 | 10/2010 | Kassab |
| 7,819,866 | B2 | 10/2010 | Bednarek |
| 7,822,460 | B2 | 10/2010 | Halperin et al. |
| 7,828,837 | B2 | 11/2010 | Khoury |
| 7,832,407 | B2 | 11/2010 | Gertner |
| 7,833,220 | B2 | 11/2010 | Mon et al. |
| 7,837,676 | B2 | 11/2010 | Sinelnikov et al. |
| 7,837,720 | B2 | 11/2010 | Mon |
| 7,841,978 | B2 | 11/2010 | Gertner |
| 7,846,157 | B2 | 12/2010 | Kozel |
| 7,846,160 | B2 | 12/2010 | Payne et al. |
| 7,846,172 | B2 | 12/2010 | Makower |
| 7,849,860 | B2 | 12/2010 | Makower et al. |
| 7,850,685 | B2 | 12/2010 | Kunis et al. |
| 7,853,333 | B2 | 12/2010 | Demarais |
| 7,854,734 | B2 | 12/2010 | Biggs et al. |
| 7,857,756 | B2 | 12/2010 | Warren et al. |
| 7,862,565 | B2 | 1/2011 | Eder et al. |
| 7,863,897 | B2 | 1/2011 | Slocum, Jr. et al. |
| 7,869,854 | B2 | 1/2011 | Shachar et al. |
| 7,873,417 | B2 | 1/2011 | Demarais et al. |
| 7,887,538 | B2 | 2/2011 | Bleich et al. |
| 7,894,905 | B2 | 2/2011 | Pless et al. |
| 7,896,873 | B2 | 3/2011 | Hiller et al. |
| 7,901,400 | B2 | 3/2011 | Wham et al. |
| 7,901,402 | B2 | 3/2011 | Jones et al. |
| 7,901,420 | B2 | 3/2011 | Dunn |
| 7,905,862 | B2 | 3/2011 | Sampson |
| 7,918,850 | B2 | 4/2011 | Govari et al. |
| 7,927,370 | B2 | 4/2011 | Webler et al. |
| 7,937,143 | B2 | 5/2011 | Demarais et al. |
| 7,938,830 | B2 | 5/2011 | Saadat et al. |
| 7,942,874 | B2 | 5/2011 | Eder et al. |
| 7,942,928 | B2 | 5/2011 | Webler et al. |
| 7,946,976 | B2 | 5/2011 | Gertner |
| 7,950,397 | B2 | 5/2011 | Thapliyal et al. |
| 7,955,293 | B2 | 6/2011 | Nita et al. |
| 7,956,613 | B2 | 6/2011 | Wald |
| 7,959,627 | B2 | 6/2011 | Utley et al. |
| 7,962,854 | B2 | 6/2011 | Vance et al. |
| 7,967,782 | B2 | 6/2011 | Laufer et al. |
| 7,967,808 | B2 | 6/2011 | Fitzgerald et al. |
| 7,972,327 | B2 | 7/2011 | Eberl et al. |
| 7,972,330 | B2 | 7/2011 | Alejandro et al. |
| 7,983,751 | B2 | 7/2011 | Zdeblick et al. |
| 8,001,976 | B2 | 8/2011 | Gertner |
| 8,007,440 | B2 | 8/2011 | Magnin et al. |
| 8,012,147 | B2 | 9/2011 | Lafontaine |
| 8,019,435 | B2 | 9/2011 | Hastings et al. |
| 8,021,362 | B2 | 9/2011 | Deem et al. |
| 8,021,413 | B2 | 9/2011 | Dierking et al. |
| 8,025,661 | B2 | 9/2011 | Arnold et al. |
| 8,027,718 | B2 | 9/2011 | Spinner et al. |
| 8,031,927 | B2 | 10/2011 | Karl et al. |
| 8,033,284 | B2 | 10/2011 | Porter et al. |
| 8,048,144 | B2 | 11/2011 | Thistle et al. |
| 8,052,636 | B2 | 11/2011 | Moll et al. |
| 8,052,700 | B2 | 11/2011 | Dunn |
| 8,062,289 | B2 | 11/2011 | Babaev |
| 8,075,580 | B2 | 12/2011 | Makower |
| 8,080,006 | B2 | 12/2011 | Lafontaine et al. |
| 8,088,127 | B2 | 1/2012 | Mayse et al. |
| 8,116,883 | B2 | 2/2012 | Williams et al. |
| 8,119,183 | B2 | 2/2012 | O'Donoghue et al. |
| 8,120,518 | B2 | 2/2012 | Jang et al. |
| 8,123,741 | B2 | 2/2012 | Marrouche et al. |
| 8,128,617 | B2 | 3/2012 | Bencini et al. |
| 8,131,371 | B2 | 3/2012 | Demarals et al. |
| 8,131,372 | B2 | 3/2012 | Levin et al. |
| 8,131,382 | B2 | 3/2012 | Asada |
| 8,137,274 | B2 | 3/2012 | Weng et al. |
| 8,140,170 | B2 | 3/2012 | Rezai et al. |
| 8,143,316 | B2 | 3/2012 | Ueno |
| 8,145,316 | B2 | 3/2012 | Deem et al. |
| 8,145,317 | B2 | 3/2012 | Demarais et al. |
| 8,150,518 | B2 | 4/2012 | Levin et al. |
| 8,150,519 | B2 | 4/2012 | Demarais et al. |
| 8,150,520 | B2 | 4/2012 | Demarais et al. |
| 8,152,830 | B2 | 4/2012 | Gumm |
| 8,162,933 | B2 | 4/2012 | Francischelli et al. |
| 8,175,711 | B2 | 5/2012 | Demarais et al. |
| 8,187,261 | B2 | 5/2012 | Watson |
| 8,190,238 | B2 | 5/2012 | Moll et al. |
| 8,192,053 | B2 | 6/2012 | Owen et al. |
| 8,198,611 | B2 | 6/2012 | LaFontaine et al. |
| 8,214,056 | B2 | 7/2012 | Hoffer et al. |
| 8,221,407 | B2 | 7/2012 | Phan et al. |
| 8,226,637 | B2 | 7/2012 | Satake |
| 8,231,617 | B2 | 7/2012 | Satake |
| 8,241,217 | B2 | 8/2012 | Chiang et al. |
| 8,257,724 | B2 | 9/2012 | Cromack et al. |
| 8,257,725 | B2 | 9/2012 | Cromack et al. |
| 8,260,397 | B2 | 9/2012 | Ruff et al. |
| 8,263,104 | B2 | 9/2012 | Ho et al. |
| 8,273,023 | B2 | 9/2012 | Razavi |
| 8,277,379 | B2 | 10/2012 | Lau et al. |
| 8,287,524 | B2 | 10/2012 | Siegel |
| 8,287,532 | B2 | 10/2012 | Carroll et al. |
| 8,292,881 | B2 | 10/2012 | Brannan et al. |
| 8,293,703 | B2 | 10/2012 | Averback et al. |
| 8,295,902 | B2 | 10/2012 | Salahieh et al. |
| 8,295,912 | B2 | 10/2012 | Gertner |
| 8,308,722 | B2 | 11/2012 | Ormsby et al. |
| 8,317,776 | B2 | 11/2012 | Ferren et al. |
| 8,317,810 | B2 | 11/2012 | Stangenes et al. |
| 8,329,179 | B2 | 12/2012 | Ni et al. |
| 8,336,705 | B2 | 12/2012 | Okahisa |
| 8,343,031 | B2 | 1/2013 | Gertner |
| 8,343,145 | B2 | 1/2013 | Brannan |
| 8,347,891 | B2 | 1/2013 | Demarais et al. |
| 8,353,945 | B2 | 1/2013 | Andreas et al. |
| 8,364,237 | B2 | 1/2013 | Stone et al. |
| 8,366,615 | B2 | 2/2013 | Razavi |
| 8,382,697 | B2 | 2/2013 | Brenneman et al. |
| 8,388,680 | B2 | 3/2013 | Starksen et al. |
| 8,396,548 | B2 | 3/2013 | Perry et al. |
| 8,398,629 | B2 | 3/2013 | Thistle |
| 8,401,667 | B2 | 3/2013 | Gustus et al. |
| 8,403,881 | B2 | 3/2013 | Ferren et al. |
| 8,406,877 | B2 | 3/2013 | Smith et al. |
| 8,409,172 | B2 | 4/2013 | Moll et al. |
| 8,409,193 | B2 | 4/2013 | Young et al. |
| 8,409,195 | B2 | 4/2013 | Young |
| 8,418,362 | B2 | 4/2013 | Zerfas et al. |
| 8,452,988 | B2 | 5/2013 | Wang |

(56) References Cited

U.S. PATENT DOCUMENTS

| | | |
|---|---|---|
| 8,454,594 B2 | 6/2013 | Demarais et al. |
| 8,460,358 B2 | 6/2013 | Andreas et al. |
| 8,465,452 B2 | 6/2013 | Kassab |
| 8,469,919 B2 | 6/2013 | Ingle et al. |
| 8,473,067 B2 | 6/2013 | Hastings et al. |
| 8,480,663 B2 | 7/2013 | Ingle et al. |
| 8,485,992 B2 | 7/2013 | Griffin et al. |
| 8,486,060 B2 | 7/2013 | Kotmel et al. |
| 8,486,063 B2 | 7/2013 | Werneth et al. |
| 8,488,591 B2 | 7/2013 | Miali et al. |
| 2001/0007070 A1 | 7/2001 | Stewart et al. |
| 2001/0039419 A1 | 11/2001 | Francischelli et al. |
| 2001/0051774 A1 | 12/2001 | Littrup et al. |
| 2002/0022864 A1 | 2/2002 | Mahvi et al. |
| 2002/0042639 A1 | 4/2002 | Murphy-Chutorian et al. |
| 2002/0045811 A1 | 4/2002 | Kittrell et al. |
| 2002/0045890 A1 | 4/2002 | Celliers et al. |
| 2002/0062146 A1 | 5/2002 | Makower et al. |
| 2002/0065542 A1 | 5/2002 | Lax et al. |
| 2002/0072686 A1 | 6/2002 | Hoey et al. |
| 2002/0077592 A1 | 6/2002 | Barry |
| 2002/0087151 A1 | 7/2002 | Mody et al. |
| 2002/0087156 A1 | 7/2002 | Maguire et al. |
| 2002/0095197 A1 | 7/2002 | Lardo et al. |
| 2002/0107511 A1 | 8/2002 | Collins et al. |
| 2002/0107536 A1 | 8/2002 | Hussein |
| 2002/0143324 A1 | 10/2002 | Edwards |
| 2002/0147480 A1 | 10/2002 | Mamayek |
| 2002/0169444 A1 | 11/2002 | Mest et al. |
| 2002/0198520 A1 | 12/2002 | Coen et al. |
| 2003/0004510 A1 | 1/2003 | Wham et al. |
| 2003/0028114 A1 | 2/2003 | Casscells, III et al. |
| 2003/0060857 A1 | 3/2003 | Perrson et al. |
| 2003/0060858 A1 | 3/2003 | Kieval et al. |
| 2003/0065317 A1 | 4/2003 | Rudie et al. |
| 2003/0069619 A1 | 4/2003 | Fenn et al. |
| 2003/0088189 A1 | 5/2003 | Tu et al. |
| 2003/0092995 A1 | 5/2003 | Thompson |
| 2003/0139689 A1 | 7/2003 | Shturman et al. |
| 2003/0195501 A1 | 10/2003 | Sherman et al. |
| 2003/0199747 A1 | 10/2003 | Michlitsch et al. |
| 2003/0212394 A1 | 11/2003 | Pearson et al. |
| 2003/0220639 A1 | 11/2003 | Chapelson et al. |
| 2003/0229340 A1 | 12/2003 | Sherry et al. |
| 2003/0229384 A1 | 12/2003 | Mon |
| 2004/0006333 A1 | 1/2004 | Arnold et al. |
| 2004/0010118 A1 | 1/2004 | Zerhusen et al. |
| 2004/0019348 A1 | 1/2004 | Stevens et al. |
| 2004/0024371 A1 | 2/2004 | Plicchi et al. |
| 2004/0043030 A1 | 3/2004 | Griffiths et al. |
| 2004/0062852 A1 | 4/2004 | Schroeder et al. |
| 2004/0064090 A1 | 4/2004 | Keren et al. |
| 2004/0073206 A1 | 4/2004 | Foley et al. |
| 2004/0088002 A1 | 5/2004 | Boyle et al. |
| 2004/0093055 A1 | 5/2004 | Bartorelli et al. |
| 2004/0106871 A1 | 6/2004 | Hunyor et al. |
| 2004/0111016 A1 | 6/2004 | Casscells, III et al. |
| 2004/0117032 A1 | 6/2004 | Roth |
| 2004/0147915 A1 | 7/2004 | Hasebe |
| 2004/0162555 A1 | 8/2004 | Farley et al. |
| 2004/0167506 A1 | 8/2004 | Chen |
| 2004/0181165 A1 | 9/2004 | Hoey et al. |
| 2004/0186356 A1 | 9/2004 | O'Malley et al. |
| 2004/0186468 A1 | 9/2004 | Edwards |
| 2004/0187875 A1 | 9/2004 | He et al. |
| 2004/0193211 A1 | 9/2004 | Voegele et al. |
| 2004/0220556 A1 | 11/2004 | Cooper et al. |
| 2004/0243022 A1 | 12/2004 | Carney et al. |
| 2004/0243199 A1 | 12/2004 | Mon et al. |
| 2004/0253304 A1 | 12/2004 | Gross et al. |
| 2004/0267250 A1 | 12/2004 | Yon et al. |
| 2005/0010095 A1 | 1/2005 | Stewart et al. |
| 2005/0010208 A1 | 1/2005 | Winston et al. |
| 2005/0015125 A1 | 1/2005 | Mioduski et al. |
| 2005/0080374 A1 | 4/2005 | Esch et al. |
| 2005/0096647 A1 | 5/2005 | Steinke et al. |
| 2005/0129616 A1 | 6/2005 | Salcedo et al. |
| 2005/0137180 A1 | 6/2005 | Robinson et al. |
| 2005/0143817 A1 | 6/2005 | Hunter et al. |
| 2005/0148842 A1 | 7/2005 | Wang et al. |
| 2005/0149069 A1 | 7/2005 | Bertolero et al. |
| 2005/0149080 A1 | 7/2005 | Hunter et al. |
| 2005/0149158 A1 | 7/2005 | Hunter et al. |
| 2005/0149173 A1 | 7/2005 | Hunter et al. |
| 2005/0149175 A1 | 7/2005 | Hunter et al. |
| 2005/0154277 A1 | 7/2005 | Tang et al. |
| 2005/0154445 A1 | 7/2005 | Hunter et al. |
| 2005/0154453 A1 | 7/2005 | Hunter et al. |
| 2005/0154454 A1 | 7/2005 | Hunter et al. |
| 2005/0165389 A1 | 7/2005 | Swain et al. |
| 2005/0165391 A1 | 7/2005 | Maguire et al. |
| 2005/0165467 A1 | 7/2005 | Hunter et al. |
| 2005/0165488 A1 | 7/2005 | Hunter et al. |
| 2005/0175661 A1 | 8/2005 | Hunter et al. |
| 2005/0175662 A1 | 8/2005 | Hunter et al. |
| 2005/0175663 A1 | 8/2005 | Hunter et al. |
| 2005/0177103 A1 | 8/2005 | Hunter et al. |
| 2005/0177225 A1 | 8/2005 | Hunter et al. |
| 2005/0181004 A1 | 8/2005 | Hunter et al. |
| 2005/0181008 A1 | 8/2005 | Hunter et al. |
| 2005/0181011 A1 | 8/2005 | Hunter et al. |
| 2005/0181977 A1 | 8/2005 | Hunter et al. |
| 2005/0182479 A1 | 8/2005 | Bonsignore et al. |
| 2005/0183728 A1 | 8/2005 | Hunter et al. |
| 2005/0186242 A1 | 8/2005 | Hunter et al. |
| 2005/0186243 A1 | 8/2005 | Hunter et al. |
| 2005/0191331 A1 | 9/2005 | Hunter et al. |
| 2005/0203410 A1 | 9/2005 | Jenkins |
| 2005/0203434 A1 | 9/2005 | Kassab |
| 2005/0203498 A1 | 9/2005 | Mon et al. |
| 2005/0209587 A1 | 9/2005 | Joye et al. |
| 2005/0214205 A1 | 9/2005 | Salcedo et al. |
| 2005/0214207 A1 | 9/2005 | Salcedo et al. |
| 2005/0214208 A1 | 9/2005 | Salcedo et al. |
| 2005/0214209 A1 | 9/2005 | Salcedo et al. |
| 2005/0214210 A1 | 9/2005 | Salcedo et al. |
| 2005/0214268 A1 | 9/2005 | Cavanagh et al. |
| 2005/0228286 A1 | 10/2005 | Messerly et al. |
| 2005/0228415 A1 | 10/2005 | Gertner |
| 2005/0228460 A1 | 10/2005 | Levin et al. |
| 2005/0232921 A1 | 10/2005 | Rosen et al. |
| 2005/0234312 A1 | 10/2005 | Suzuki et al. |
| 2005/0245862 A1 | 11/2005 | Seward |
| 2005/0251116 A1 | 11/2005 | Steinke et al. |
| 2005/0252553 A1 | 11/2005 | Ginggen |
| 2005/0256398 A1 | 11/2005 | Hastings et al. |
| 2005/0267556 A1 | 12/2005 | Shuros et al. |
| 2005/0283195 A1 | 12/2005 | Pastore et al. |
| 2006/0004323 A1 | 1/2006 | Chang et al. |
| 2006/0018949 A1 | 1/2006 | Ammon et al. |
| 2006/0024564 A1 | 2/2006 | Manclaw |
| 2006/0025765 A1 | 2/2006 | Landman et al. |
| 2006/0062786 A1 | 3/2006 | Salcedo et al. |
| 2006/0083194 A1 | 4/2006 | Dhrimaj et al. |
| 2006/0085054 A1 | 4/2006 | Zikorus et al. |
| 2006/0089637 A1 | 4/2006 | Werneth et al. |
| 2006/0089638 A1 | 4/2006 | Carmel |
| 2006/0095096 A1 | 5/2006 | DeBenedictis et al. |
| 2006/0106375 A1 | 5/2006 | Werneth et al. |
| 2006/0142790 A1 | 6/2006 | Gertner |
| 2006/0147492 A1 | 7/2006 | Hunter et al. |
| 2006/0167106 A1 | 7/2006 | Zhang et al. |
| 2006/0167498 A1 | 7/2006 | DiLorenzo |
| 2006/0171895 A1 | 8/2006 | Bucay-Couto |
| 2006/0184060 A1 | 8/2006 | Belacazar et al. |
| 2006/0184221 A1 | 8/2006 | Stewart et al. |
| 2006/0195139 A1 | 8/2006 | Gertner |
| 2006/0206150 A1 | 9/2006 | Demarais et al. |
| 2006/0224153 A1 | 10/2006 | Fischell et al. |
| 2006/0235286 A1 | 10/2006 | Stone et al. |
| 2006/0239921 A1 | 10/2006 | Mangat et al. |
| 2006/0240070 A1 | 10/2006 | Cromack et al. |
| 2006/0246143 A1 | 11/2006 | Ege |
| 2006/0247266 A1 | 11/2006 | Yamada et al. |

(56) References Cited

U.S. PATENT DOCUMENTS

| | | |
|---|---|---|
| 2006/0247617 A1* | 11/2006 | Danek et al. .................. 606/41 |
| 2006/0247760 A1 | 11/2006 | Ganesan et al. |
| 2006/0263393 A1 | 11/2006 | Demopulos et al. |
| 2006/0269555 A1 | 11/2006 | Salcedo et al. |
| 2006/0271111 A1 | 11/2006 | Demarais et al. |
| 2006/0287644 A1 | 12/2006 | Inganas et al. |
| 2007/0016184 A1 | 1/2007 | Cropper et al. |
| 2007/0016274 A1 | 1/2007 | Boveja et al. |
| 2007/0027390 A1 | 2/2007 | Maschke et al. |
| 2007/0043077 A1 | 2/2007 | Mewshaw et al. |
| 2007/0043409 A1 | 2/2007 | Brian et al. |
| 2007/0049924 A1 | 3/2007 | Rahn |
| 2007/0066972 A1 | 3/2007 | Ormsby et al. |
| 2007/0073151 A1 | 3/2007 | Lee |
| 2007/0078498 A1 | 4/2007 | Rezai et al. |
| 2007/0093710 A1 | 4/2007 | Maschke |
| 2007/0100405 A1 | 5/2007 | Thompson et al. |
| 2007/0106247 A1 | 5/2007 | Burnett et al. |
| 2007/0112327 A1 | 5/2007 | Yun et al. |
| 2007/0118107 A1 | 5/2007 | Francischelli et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0149963 A1 | 6/2007 | Matsukuma et al. |
| 2007/0162109 A1 | 7/2007 | Davila et al. |
| 2007/0173805 A1 | 7/2007 | Weinberg et al. |
| 2007/0173899 A1 | 7/2007 | Levin et al. |
| 2007/0179496 A1 | 8/2007 | Swoyer et al. |
| 2007/0197891 A1 | 8/2007 | Shachar et al. |
| 2007/0203480 A1 | 8/2007 | Mody et al. |
| 2007/0207186 A1 | 9/2007 | Scanlon et al. |
| 2007/0208134 A1 | 9/2007 | Hunter et al. |
| 2007/0208210 A1 | 9/2007 | Gelfand et al. |
| 2007/0208256 A1 | 9/2007 | Marilla |
| 2007/0208301 A1 | 9/2007 | Evard et al. |
| 2007/0219576 A1 | 9/2007 | Cangialosi |
| 2007/0225781 A1 | 9/2007 | Saadat et al. |
| 2007/0233170 A1 | 10/2007 | Gertner |
| 2007/0239062 A1 | 10/2007 | Chopra et al. |
| 2007/0244423 A1* | 10/2007 | Zumeris ............ A61M 25/0017 604/22 |
| 2007/0248639 A1 | 10/2007 | Demopulos et al. |
| 2007/0249703 A1 | 10/2007 | Mewshaw et al. |
| 2007/0254833 A1 | 11/2007 | Hunter et al. |
| 2007/0265687 A1 | 11/2007 | Deem et al. |
| 2007/0278103 A1 | 12/2007 | Hoerret et al. |
| 2007/0282302 A1 | 12/2007 | Wachsman et al. |
| 2007/0292411 A1 | 12/2007 | Salcedo et al. |
| 2007/0293782 A1 | 12/2007 | Marino |
| 2007/0299043 A1 | 12/2007 | Hunter et al. |
| 2008/0004673 A1 | 1/2008 | Rossing et al. |
| 2008/0009927 A1 | 1/2008 | Vilims |
| 2008/0015501 A1 | 1/2008 | Gertner |
| 2008/0021408 A1 | 1/2008 | Jacobsen et al. |
| 2008/0033049 A1 | 2/2008 | Mewshaw |
| 2008/0033465 A1* | 2/2008 | Schmitz et al. ............... 606/170 |
| 2008/0039746 A1 | 2/2008 | Hissong et al. |
| 2008/0039830 A1 | 2/2008 | Munger et al. |
| 2008/0051454 A1 | 2/2008 | Wang |
| 2008/0051812 A1* | 2/2008 | Schmitz et al. ............... 606/167 |
| 2008/0064957 A1 | 3/2008 | Spence |
| 2008/0071269 A1 | 3/2008 | Hilario et al. |
| 2008/0071306 A1 | 3/2008 | Gertner |
| 2008/0082109 A1 | 4/2008 | Moll et al. |
| 2008/0086072 A1 | 4/2008 | Bonutti et al. |
| 2008/0091193 A1 | 4/2008 | Kauphusman et al. |
| 2008/0097251 A1 | 4/2008 | Babaev |
| 2008/0097426 A1 | 4/2008 | Root et al. |
| 2008/0108867 A1 | 5/2008 | Zhou |
| 2008/0119879 A1 | 5/2008 | Brenneman et al. |
| 2008/0125772 A1 | 5/2008 | Stone et al. |
| 2008/0132450 A1 | 6/2008 | Lee et al. |
| 2008/0140002 A1 | 6/2008 | Ramzipoor et al. |
| 2008/0147002 A1 | 6/2008 | Gertner |
| 2008/0161662 A1 | 7/2008 | Golijanin et al. |
| 2008/0161717 A1 | 7/2008 | Gertner |
| 2008/0161801 A1 | 7/2008 | Steinke et al. |
| 2008/0171974 A1 | 7/2008 | Lafontaine et al. |
| 2008/0172035 A1 | 7/2008 | Starksen et al. |
| 2008/0172104 A1 | 7/2008 | Kieval et al. |
| 2008/0188912 A1 | 8/2008 | Stone et al. |
| 2008/0188913 A1* | 8/2008 | Stone et al. .................. 607/99 |
| 2008/0208162 A1 | 8/2008 | Joshi |
| 2008/0208169 A1 | 8/2008 | Boyle et al. |
| 2008/0213331 A1 | 9/2008 | Gelfand et al. |
| 2008/0215117 A1 | 9/2008 | Gross |
| 2008/0221448 A1 | 9/2008 | Khuri-Yakub et al. |
| 2008/0234790 A1 | 9/2008 | Bayer et al. |
| 2008/0243091 A1 | 10/2008 | Humphreys et al. |
| 2008/0245371 A1 | 10/2008 | Gruber |
| 2008/0249525 A1 | 10/2008 | Lee et al. |
| 2008/0249547 A1 | 10/2008 | Dunn |
| 2008/0255550 A1 | 10/2008 | Bell |
| 2008/0255642 A1 | 10/2008 | Zarins et al. |
| 2008/0262412 A1* | 10/2008 | Atanasoska ............ A61N 1/325 604/20 |
| 2008/0262489 A1 | 10/2008 | Steinke |
| 2008/0269664 A1* | 10/2008 | Trovato et al. .................. 604/20 |
| 2008/0275484 A1 | 11/2008 | Gertner |
| 2008/0281312 A1 | 11/2008 | Werneth et al. |
| 2008/0281347 A1 | 11/2008 | Gertner |
| 2008/0287918 A1 | 11/2008 | Rosenman et al. |
| 2008/0294037 A1 | 11/2008 | Richter |
| 2008/0300618 A1 | 12/2008 | Gertner |
| 2008/0312644 A1 | 12/2008 | Fourkas et al. |
| 2008/0312673 A1 | 12/2008 | Viswanathan et al. |
| 2008/0317818 A1 | 12/2008 | Griffith et al. |
| 2009/0018486 A1 | 1/2009 | Goren et al. |
| 2009/0018609 A1 | 1/2009 | DiLorenzo |
| 2009/0024194 A1 | 1/2009 | Arcot-Krishnamurthy et al. |
| 2009/0030312 A1 | 1/2009 | Hadjicostis |
| 2009/0036948 A1 | 2/2009 | Levin et al. |
| 2009/0043372 A1 | 2/2009 | Northrop et al. |
| 2009/0054082 A1 | 2/2009 | Kim et al. |
| 2009/0062873 A1 | 3/2009 | Wu et al. |
| 2009/0069671 A1 | 3/2009 | Anderson |
| 2009/0074828 A1 | 3/2009 | Alexis et al. |
| 2009/0076409 A1 | 3/2009 | Wu et al. |
| 2009/0088735 A1 | 4/2009 | Abboud et al. |
| 2009/0105631 A1 | 4/2009 | Kieval |
| 2009/0112202 A1 | 4/2009 | Young |
| 2009/0118620 A1 | 5/2009 | Tgavalekos et al. |
| 2009/0118726 A1* | 5/2009 | Auth .................. A61B 18/1492 606/33 |
| 2009/0125099 A1 | 5/2009 | Weber et al. |
| 2009/0131798 A1 | 5/2009 | Minar et al. |
| 2009/0143640 A1 | 6/2009 | Saadat et al. |
| 2009/0156988 A1 | 6/2009 | Ferren et al. |
| 2009/0157057 A1 | 6/2009 | Ferren et al. |
| 2009/0157161 A1 | 6/2009 | Desai et al. |
| 2009/0171333 A1 | 7/2009 | Hon |
| 2009/0192558 A1 | 7/2009 | Whitehurst et al. |
| 2009/0198223 A1 | 8/2009 | Thilwind et al. |
| 2009/0203962 A1 | 8/2009 | Miller et al. |
| 2009/0203993 A1 | 8/2009 | Mangat et al. |
| 2009/0204170 A1 | 8/2009 | Hastings et al. |
| 2009/0210953 A1 | 8/2009 | Moyer et al. |
| 2009/0216317 A1 | 8/2009 | Cromack et al. |
| 2009/0221955 A1 | 9/2009 | Babaev |
| 2009/0226429 A1 | 9/2009 | Salcedo et al. |
| 2009/0240249 A1 | 9/2009 | Chan et al. |
| 2009/0247933 A1 | 10/2009 | Maor et al. |
| 2009/0247966 A1 | 10/2009 | Gunn et al. |
| 2009/0248012 A1 | 10/2009 | Maor et al. |
| 2009/0253974 A1 | 10/2009 | Rahme |
| 2009/0264755 A1 | 10/2009 | Chen et al. |
| 2009/0270850 A1 | 10/2009 | Zhou et al. |
| 2009/0281533 A1 | 11/2009 | Ingle et al. |
| 2009/0287137 A1 | 11/2009 | Crowley |
| 2009/0318749 A1 | 12/2009 | Stolen et al. |
| 2010/0009267 A1 | 1/2010 | Chase et al. |
| 2010/0049191 A1 | 1/2010 | Habib et al. |
| 2010/0030061 A1 | 2/2010 | Canfield et al. |
| 2010/0048983 A1 | 2/2010 | Ball et al. |

(56) References Cited

U.S. PATENT DOCUMENTS

| | | |
|---|---|---|
| 2010/0049099 A1 | 2/2010 | Thapliyal et al. |
| 2010/0049186 A1 | 2/2010 | Ingle et al. |
| 2010/0049188 A1 | 2/2010 | Nelson et al. |
| 2010/0049283 A1 | 2/2010 | Johnson |
| 2010/0069837 A1 | 3/2010 | Rassat et al. |
| 2010/0076299 A1 | 3/2010 | Gustus et al. |
| 2010/0076425 A1 | 3/2010 | Carroux |
| 2010/0087782 A1 | 4/2010 | Ghaffari et al. |
| 2010/0106005 A1 | 4/2010 | Karczmar et al. |
| 2010/0114244 A1 | 5/2010 | Manda et al. |
| 2010/0125268 A1 | 5/2010 | Gustus et al. |
| 2010/0130836 A1 | 5/2010 | Malchano et al. |
| 2010/0137860 A1 | 6/2010 | Demarais et al. |
| 2010/0137952 A1 | 6/2010 | Demarais et al. |
| 2010/0160903 A1 | 6/2010 | Krespi |
| 2010/0160906 A1 | 6/2010 | Jarrard |
| 2010/0168624 A1 | 7/2010 | Sliwa |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0191112 A1 | 7/2010 | Demarais et al. |
| 2010/0191232 A1 | 7/2010 | Boveda |
| 2010/0204560 A1 | 8/2010 | Salahieh et al. |
| 2010/0217162 A1 | 8/2010 | Hissong et al. |
| 2010/0222786 A1 | 9/2010 | Kassab |
| 2010/0222851 A1 | 9/2010 | Deem et al. |
| 2010/0222854 A1 | 9/2010 | Demarais et al. |
| 2010/0228122 A1 | 9/2010 | Keenan et al. |
| 2010/0249604 A1 | 9/2010 | Hastings et al. |
| 2010/0249773 A1 | 9/2010 | Clark et al. |
| 2010/0256616 A1 | 10/2010 | Katoh et al. |
| 2010/0268217 A1 | 10/2010 | Habib |
| 2010/0268307 A1 | 10/2010 | Demarais et al. |
| 2010/0284927 A1 | 11/2010 | Lu et al. |
| 2010/0286684 A1 | 11/2010 | Hata et al. |
| 2010/0298821 A1 | 11/2010 | Garbagnati |
| 2010/0305036 A1 | 12/2010 | Barnes et al. |
| 2010/0312141 A1 | 12/2010 | Keast et al. |
| 2010/0324472 A1 | 12/2010 | Wulfman |
| 2011/0009750 A1 | 1/2011 | Taylor et al. |
| 2011/0021976 A1 | 1/2011 | Li et al. |
| 2011/0034832 A1 | 2/2011 | Cioanta et al. |
| 2011/0040324 A1 | 2/2011 | McCarthy et al. |
| 2011/0044942 A1 | 2/2011 | Puri et al. |
| 2011/0060324 A1 | 3/2011 | Wu et al. |
| 2011/0071400 A1 | 3/2011 | Hastings et al. |
| 2011/0071401 A1 | 3/2011 | Hastings et al. |
| 2011/0077498 A1 | 3/2011 | McDaniel |
| 2011/0092781 A1 | 4/2011 | Gertner |
| 2011/0092880 A1 | 4/2011 | Gertner |
| 2011/0104061 A1 | 5/2011 | Seward |
| 2011/0112400 A1 | 5/2011 | Emery et al. |
| 2011/0118598 A1 | 5/2011 | Gertner |
| 2011/0118600 A1 | 5/2011 | Gertner |
| 2011/0118726 A1 | 5/2011 | De La Rama et al. |
| 2011/0130708 A1 | 6/2011 | Perry et al. |
| 2011/0137155 A1 | 6/2011 | Weber et al. |
| 2011/0144479 A1 | 6/2011 | Hastings et al. |
| 2011/0146673 A1 | 6/2011 | Keast et al. |
| 2011/0166499 A1 | 7/2011 | Demarais et al. |
| 2011/0178403 A1 | 7/2011 | Weng et al. |
| 2011/0178570 A1 | 7/2011 | Demarais |
| 2011/0200171 A1 | 8/2011 | Beetel et al. |
| 2011/0202098 A1 | 8/2011 | Demarais et al. |
| 2011/0207758 A1 | 8/2011 | Sobotka et al. |
| 2011/0208096 A1 | 8/2011 | Demarais et al. |
| 2011/0257523 A1 | 10/2011 | Hastings et al. |
| 2011/0257564 A1 | 10/2011 | Demarais et al. |
| 2011/0257622 A1 | 10/2011 | Salahieh et al. |
| 2011/0257641 A1 | 10/2011 | Hastings et al. |
| 2011/0257642 A1 | 10/2011 | Griggs, III |
| 2011/0263921 A1 | 10/2011 | Vrba et al. |
| 2011/0264011 A1 | 10/2011 | Wu et al. |
| 2011/0264075 A1 | 10/2011 | Leung et al. |
| 2011/0264086 A1 | 10/2011 | Ingle |
| 2011/0264116 A1 | 10/2011 | Kocur et al. |
| 2011/0270238 A1 | 11/2011 | Rizq et al. |
| 2011/0306851 A1 | 12/2011 | Wang |
| 2011/0307034 A1 | 12/2011 | Hastings et al. |
| 2011/0319809 A1 | 12/2011 | Smith |
| 2012/0029496 A1 | 2/2012 | Smith |
| 2012/0029500 A1 | 2/2012 | Jenson |
| 2012/0029505 A1 | 2/2012 | Jenson |
| 2012/0029509 A1 | 2/2012 | Smith |
| 2012/0029510 A1 | 2/2012 | Haverkost |
| 2012/0029511 A1 | 2/2012 | Smith et al. |
| 2012/0029512 A1 | 2/2012 | Willard et al. |
| 2012/0029513 A1 | 2/2012 | Smith et al. |
| 2012/0059241 A1 | 3/2012 | Hastings et al. |
| 2012/0059286 A1 | 3/2012 | Hastings et al. |
| 2012/0065506 A1 | 3/2012 | Smith |
| 2012/0065554 A1 | 3/2012 | Pikus |
| 2012/0095461 A1 | 4/2012 | Herscher et al. |
| 2012/0101413 A1 | 4/2012 | Beetel et al. |
| 2012/0101490 A1 | 4/2012 | Smith |
| 2012/0101538 A1 | 4/2012 | Ballakur et al. |
| 2012/0109021 A1 | 5/2012 | Hastings et al. |
| 2012/0116382 A1 | 5/2012 | Ku et al. |
| 2012/0116383 A1 | 5/2012 | Mauch et al. |
| 2012/0116392 A1 | 5/2012 | Willard |
| 2012/0116438 A1 | 5/2012 | Salahieh et al. |
| 2012/0116486 A1 | 5/2012 | Naga et al. |
| 2012/0123243 A1 | 5/2012 | Hastings |
| 2012/0123258 A1 | 5/2012 | Willard |
| 2012/0123261 A1 | 5/2012 | Jenson et al. |
| 2012/0123303 A1 | 5/2012 | Sogard et al. |
| 2012/0123406 A1 | 5/2012 | Edmunds et al. |
| 2012/0130289 A1 | 5/2012 | Demarais et al. |
| 2012/0130345 A1 | 5/2012 | Levin et al. |
| 2012/0130359 A1 | 5/2012 | Turovskiy |
| 2012/0130360 A1 | 5/2012 | Buckley et al. |
| 2012/0130362 A1 | 5/2012 | Hastings et al. |
| 2012/0130368 A1 | 5/2012 | Jenson |
| 2012/0130458 A1 | 5/2012 | Ryba et al. |
| 2012/0136344 A1 | 5/2012 | Buckley et al. |
| 2012/0136349 A1 | 5/2012 | Hastings |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143181 A1 | 6/2012 | Demarais et al. |
| 2012/0143293 A1 | 6/2012 | Mauch et al. |
| 2012/0143294 A1 | 6/2012 | Clark et al. |
| 2012/0150267 A1 | 6/2012 | Buckley et al. |
| 2012/0157986 A1 | 6/2012 | Stone et al. |
| 2012/0157987 A1 | 6/2012 | Steinke et al. |
| 2012/0157988 A1 | 6/2012 | Stone et al. |
| 2012/0157989 A1 | 6/2012 | Stone et al. |
| 2012/0157992 A1 | 6/2012 | Smith et al. |
| 2012/0157993 A1 | 6/2012 | Jenson et al. |
| 2012/0158101 A1 | 6/2012 | Stone et al. |
| 2012/0158104 A1 | 6/2012 | Huynh et al. |
| 2012/0172837 A1 | 7/2012 | Demarais et al. |
| 2012/0172870 A1 | 7/2012 | Jenson et al. |
| 2012/0184952 A1 | 7/2012 | Jenson et al. |
| 2012/0197198 A1 | 8/2012 | Demarais et al. |
| 2012/0197252 A1 | 8/2012 | Deem et al. |
| 2012/0232409 A1 | 9/2012 | Stahmann et al. |
| 2012/0265066 A1 | 10/2012 | Crow et al. |
| 2012/0265198 A1 | 10/2012 | Crow et al. |
| 2013/0012844 A1 | 1/2013 | Demarais et al. |
| 2013/0012866 A1 | 1/2013 | Deem et al. |
| 2013/0012867 A1 | 1/2013 | Demarais et al. |
| 2013/0013024 A1 | 1/2013 | Levin et al. |
| 2013/0023865 A1 | 1/2013 | Steinke et al. |
| 2013/0035681 A1 | 2/2013 | Subramaniam et al. |
| 2013/0066316 A1 | 3/2013 | Steinke et al. |
| 2013/0085489 A1 | 4/2013 | Fain et al. |
| 2013/0090563 A1 | 4/2013 | Weber |
| 2013/0090578 A1 | 4/2013 | Smith et al. |
| 2013/0090647 A1 | 4/2013 | Smith |
| 2013/0090649 A1 | 4/2013 | Smith et al. |
| 2013/0090650 A1 | 4/2013 | Jenson et al. |
| 2013/0090651 A1 | 4/2013 | Smith |
| 2013/0090652 A1 | 4/2013 | Jenson |

(56) References Cited

U.S. PATENT DOCUMENTS

| | | |
|---|---|---|
| 2013/0096550 A1 | 4/2013 | Hill |
| 2013/0096553 A1 | 4/2013 | Hill et al. |
| 2013/0096554 A1 | 4/2013 | Groff et al. |
| 2013/0096604 A1 | 4/2013 | Hanson et al. |
| 2013/0110106 A1 | 5/2013 | Richardson |
| 2013/0116687 A1 | 5/2013 | Willard |
| 2013/0165764 A1 | 6/2013 | Scheuermann et al. |
| 2013/0165844 A1 | 6/2013 | Shuros et al. |
| 2013/0165916 A1 | 6/2013 | Mathur et al. |
| 2013/0165917 A1 | 6/2013 | Mathur et al. |
| 2013/0165920 A1 | 6/2013 | Weber et al. |
| 2013/0165923 A1 | 6/2013 | Mathur et al. |
| 2013/0165924 A1 | 6/2013 | Mathur et al. |
| 2013/0165925 A1 | 6/2013 | Mathur et al. |
| 2013/0165926 A1 | 6/2013 | Mathur et al. |
| 2013/0165990 A1 | 6/2013 | Mathur et al. |
| 2013/0172815 A1 | 7/2013 | Perry et al. |
| 2013/0172872 A1 | 7/2013 | Subramaniam et al. |
| 2013/0172877 A1 | 7/2013 | Subramaniam et al. |
| 2013/0172878 A1 | 7/2013 | Smith |
| 2013/0172879 A1 | 7/2013 | Sutermeister |
| 2013/0172880 A1 | 7/2013 | Willard |
| 2013/0172881 A1 | 7/2013 | Hill et al. |

FOREIGN PATENT DOCUMENTS

| | | |
|---|---|---|
| CN | 102271607 A | 12/2011 |
| DE | 10038737 A1 | 2/2002 |
| DE | 102005041601 A1 | 4/2007 |
| DE | 102008048616 A1 | 4/2010 |
| EP | 558297 A2 | 9/1993 |
| EP | 647435 A1 | 4/1995 |
| EP | 634910 B1 | 8/1997 |
| EP | 868884 A2 | 10/1998 |
| EP | 1005838 A1 | 6/2000 |
| EP | 1053720 A1 | 11/2000 |
| EP | 1064886 A1 | 1/2001 |
| EP | 1180004 A1 | 2/2002 |
| EP | 1181895 A2 | 2/2002 |
| EP | 1297795 A1 | 6/2002 |
| EP | 1264613 A2 | 12/2002 |
| EP | 1286625 A1 | 3/2003 |
| EP | 1332724 A1 | 8/2003 |
| EP | 1335677 B1 | 8/2003 |
| EP | 866675 B1 | 10/2003 |
| EP | 1433448 A1 | 6/2004 |
| EP | 1442719 A1 | 8/2004 |
| EP | 1547537 A1 | 6/2005 |
| EP | 1622531 | 2/2006 |
| EP | 1634542 A1 | 3/2006 |
| EP | 1698296 A1 | 6/2006 |
| EP | 1709922 A1 | 10/2006 |
| EP | 1874211 A2 | 1/2008 |
| EP | 1906853 A2 | 4/2008 |
| EP | 1946712 A1 | 7/2008 |
| EP | 1961394 A2 | 8/2008 |
| EP | 1715798 B1 | 4/2009 |
| EP | 1620156 B1 | 7/2009 |
| EP | 2076193 A2 | 7/2009 |
| EP | 2091455 A2 | 8/2009 |
| EP | 2092957 A1 | 8/2009 |
| EP | 2197533 A1 | 6/2010 |
| EP | 2208506 A1 | 7/2010 |
| EP | 1579889 B1 | 8/2010 |
| EP | 2241279 A1 | 10/2010 |
| EP | 2092957 B1 | 1/2011 |
| EP | 2329859 A1 | 6/2011 |
| EP | 2349044 A1 | 8/2011 |
| EP | 2027882 B1 | 10/2011 |
| EP | 2378956 A2 | 10/2011 |
| EP | 2037840 B1 | 12/2011 |
| EP | 2204134 B1 | 4/2012 |
| EP | 2320821 B1 | 10/2012 |
| GB | 2313062 A | 11/1997 |
| GB | 2453601 A | 4/2009 |
| GB | 2456301 A | 7/2009 |
| JP | 2003510126 A | 3/2003 |
| WO | 9103207 A1 | 3/1991 |
| WO | 9117731 A1 | 11/1991 |
| WO | 9320747 A1 | 10/1993 |
| WO | 9320770 A2 | 10/1993 |
| WO | 9418896 A1 | 9/1994 |
| WO | 9428809 A1 | 12/1994 |
| WO | 9501751 A1 | 1/1995 |
| WO | 9531142 A1 | 11/1995 |
| WO | 9634559 A1 | 11/1996 |
| WO | 9703604 A1 | 2/1997 |
| WO | 9717104 A1 | 5/1997 |
| WO | 9720510 A1 | 6/1997 |
| WO | 9732532 A1 | 9/1997 |
| WO | 9740760 A1 | 11/1997 |
| WO | 9745156 A2 | 12/1997 |
| WO | 9818393 A1 | 5/1998 |
| WO | 9834565 A1 | 8/1998 |
| WO | 9835638 A1 | 8/1998 |
| WO | 9840023 A1 | 9/1998 |
| WO | 9858588 A1 | 12/1998 |
| WO | 9900060 A1 | 1/1999 |
| WO | 9916370 A1 | 4/1999 |
| WO | 9921608 A1 | 5/1999 |
| WO | 9934741 A1 | 7/1999 |
| WO | 9944522 A1 | 9/1999 |
| WO | 0010475 A1 | 3/2000 |
| WO | 0047118 A1 | 8/2000 |
| WO | 0051513 A1 | 9/2000 |
| WO | 0059394 A1 | 10/2000 |
| WO | 0062727 A1 | 10/2000 |
| WO | 0064387 A1 | 11/2000 |
| WO | 0069376 A1 | 11/2000 |
| WO | 0072909 A1 | 12/2000 |
| WO | 0122897 A1 | 4/2001 |
| WO | 0137746 A1 | 5/2001 |
| WO | 0187172 A1 | 5/2001 |
| WO | 0187154 A1 | 11/2001 |
| WO | 0195820 A1 | 12/2001 |
| WO | 0228475 A1 | 4/2002 |
| WO | 0239915 A1 | 5/2002 |
| WO | 02058549 A1 | 8/2002 |
| WO | 02080766 A2 | 10/2002 |
| WO | 02087679 A2 | 11/2002 |
| WO | 02089686 A1 | 11/2002 |
| WO | 03026525 A1 | 4/2003 |
| WO | 03077781 A1 | 9/2003 |
| WO | 2004047659 A2 | 6/2004 |
| WO | 2004049976 A1 | 6/2004 |
| WO | 2004064606 A2 | 8/2004 |
| WO | 2004069300 A2 | 8/2004 |
| WO | 2004076146 A2 | 9/2004 |
| WO | 2004098694 A1 | 11/2004 |
| WO | 2004100813 A2 | 11/2004 |
| WO | 2004105807 A2 | 12/2004 |
| WO | 2004110258 A2 | 12/2004 |
| WO | 2005007000 | 1/2005 |
| WO | 2005037070 A2 | 4/2005 |
| WO | 2005041748 A2 | 5/2005 |
| WO | 2005074829 A1 | 8/2005 |
| WO | 2006041881 A2 | 4/2006 |
| WO | 2006105121 A2 | 10/2006 |
| WO | 2006116198 A2 | 11/2006 |
| WO | 2007011634 A1 | 1/2007 |
| WO | 2007014063 A2 | 2/2007 |
| WO | 2007047870 A2 | 4/2007 |
| WO | 2007113865 A1 | 10/2007 |
| WO | 2007135431 A2 | 11/2007 |
| WO | 2007146215 A2 | 12/2007 |
| WO | 2008003058 A2 | 1/2008 |
| WO | 2008009972 A2 | 1/2008 |
| WO | 2008010150 A2 | 1/2008 |
| WO | 2008014465 A2 | 1/2008 |
| WO | 2008036281 A2 | 3/2008 |
| WO | 2008049084 A2 | 4/2008 |
| WO | 2008061152 A2 | 5/2008 |
| WO | 2008102363 A2 | 8/2008 |

(56) References Cited

FOREIGN PATENT DOCUMENTS

| WO | 2009036471 A1 | 3/2009 |
|---|---|---|
| WO | 2009082635 A1 | 7/2009 |
| WO | 2009088678 A1 | 7/2009 |
| WO | 2009113064 A2 | 9/2009 |
| WO | 2009121017 | 10/2009 |
| WO | 2009121017 A1 | 10/2009 |
| WO | 2009137819 A1 | 11/2009 |
| WO | 2010042653 A1 | 4/2010 |
| WO | 2010048007 A1 | 4/2010 |
| WO | 2010056771 A1 | 5/2010 |
| WO | 2010057043 A1 | 5/2010 |
| WO | 2010067360 A2 | 6/2010 |
| WO | 2010070766 A1 | 6/2010 |
| WO | 2010099207 A1 | 9/2010 |
| WO | 2010102310 A2 | 9/2010 |
| WO | 2010120944 A2 | 10/2010 |
| WO | 2010134503 A1 | 11/2010 |
| WO | 2011005901 A2 | 1/2011 |
| WO | 2011053757 A1 | 5/2011 |
| WO | 2011053772 A1 | 5/2011 |
| WO | 2011055143 A2 | 5/2011 |
| WO | 2011060339 A1 | 5/2011 |
| WO | 2011091069 A1 | 7/2011 |
| WO | 2011126580 A2 | 10/2011 |
| WO | 2011130534 A2 | 10/2011 |
| WO | 2012019156 A1 | 2/2012 |
| WO | 2013049601 A2 | 4/2013 |

OTHER PUBLICATIONS

"IntraLuminal: Products," IntraLuminal Therapeutics, Inc., 2003, p. 1-9.
"Laser Catheter to Aid Coronary Surgery," TechTalk: MIT, Jan. 9, 1991, p. 1-4.
"Optical Coherence Tomography: Advantages of OCT," LightLab Imaging Technology.
"Optical Coherence Tomography: Image Gallery Cardiovascular Procedures," LightLab Imaging Technology.
"Optical Coherence Tomography: LightLab Imaging Starts US Cardiology Clinical Investigations," LightLab Imaging Technology, 2002.
"Optical Coherence Tomography: LightLab Sees Bright Prospects for Cardiac Application of OCT Technology," LightLab Imaging Technology, 2001, vol. 27, No. 35.
"Optical Coherence Tomography: What is OCT?," LightLab Imaging Technology.
"Optical Coherence Tomography: Why Use OCT?," LightLab Imaging Technology.
"Products—Functional Measurement," Volcano Functional Measurement Products US, Mar. 24, 2003, p. 1-2.
Brown et al., "Radiofrequency capacitive heaters: the effect of coupling medium resistivity on power absorption along a mouse leg," Physics in Medicine and Biology, 1993, p. 1-12, vol. 38.
Carrington, "Future of CVI: It's all about plaque: Identification of vulnerable lesions, not 'rusty pipes,' could become cornerstone of preventive cardiology," Diagnostic Imaging, 2001, p. 1-8.
Chen et al., "Percutaneous pulmonary artery denervation completely abolishes experimental pulmonary arterial hypertension in vivo," EuroIntervention, 2013, p. 1-8.
Cimino, "Preventing plaque attack," Mass High Tech, 2001, p. 1-2.
Dahm et al., "Relation of Degree of Laser Debulking of In-Stent Restenosis as a Predictor of Restenosis Rate," The American Journal of Cardiology, 2002, p. 68-70, vol. 90.
De Korte et al., "Characterization of Plaque Components With Intravascular Ultrasound Elastography in Human Femoral and Coronary Arteries in Vitro," Circulation, Aug. 8, 2000, p. 617-623.
Durney et al., "Radiofrequency Radiation Dosimetry Handbook," Oct. 1986, p. 1-2, Fourth Edition.
Durney et al., "Radiofrequency Radiation Dosimetry Handbook: Contents," Oct. 1986, p. 1-5, Fourth Edition.

Fournier-Desseux et al., "Assessment of 1-lead and 2-lead electrode patterns in electrical impedance endotomography," Physiological Measurement, 2005, p. 337-349. vol. 26, Institute of Physics Publishing.
Fram et al., "Feasibility of Radiofrequency Powered, Thermal Balloon Ablation of Atrioventricular Bypass Tracts Via the Coronary Sinus: In Vivo Canine Studies," PACE, Aug. 1995, p. 1518-1530, vol. 18.
Fram et al., "Low Pressure Radiofrequency Balloon Angioplasty: Evaluation in Porcine Peripheral Arteries," JACC, 1993, p. 1512-1521, vol. 21, No. 6, American College of Cardiology.
Fujimori et al., "Significant Prevention of In-Stent Restenosis by Evans Blue in Patients with Acute Myocardial Infarction," American Heart Association, 2002.
Fujita et al., "Sarpogrelate, An Antagonist of 5-HT(2A) Receptor, Treatment Reduces Restenosis After Coronary Stenting," American Heart Association, 2002.
Gabriel, "Appendix A: Experimental Data," 1999, p. 1-21.
Gabriel, "Appendix C: Modeling the frequency dependence of the dielectric properties to a 4 dispersions spectrum," p. 1-6.
Gregory et al., "Liquid Core Light Guide for Laser Angioplasty," The Journal of Quantum Electronics, Dec. 1990, p. 2289-2296, vol. 26, No. 12.
Kaplan et al., "Healing after Arterial Dilatation with Radiofrequency Thermal and Nonthermal Balloon Angioplasty Sytems," Journal of Investigative Surgery, 1993, p. 33-52, vol. 6.
Kolata, "New Studies Question Value of Opening Arteries," The New York Times, Mar. 21, 2004, p. 1-5.
Konings et al., "Development of an Intravascular Impedance Catheter for Detection of Fatty Lesions in Arteries," IEEE Transactions on Medical Imaging, Aug. 1997, p. 439-446, vol. 16, No. 4.
Kurtz et al., "Lamellar Refractive Surgery with Scanned Intrastromal Picosecond and Femtosecond Laser Pulses in Animal Eyes," Journal of Refractive Surgery, Sep./Oct. 1998, p. 541-548.
Lee et al., "Thermal Compression and Molding of Atherosclerotic Vascular Tissue With Use of Radiofrequency Energy: Implications for Radiofrequency Balloon Angioplasty," JACC, 1989, p. 1167-1175, vol. 13, No. 5, American College of Cardiology.
Lima et al., "Efficacy and Safety of Oral Sirolimus to Treat and Prevent In-Stent Restenosis: A Pilot Study Results," American Heart Association, 2002, p. 2929.
Lima et al., "Systemic Immunosuppression Inhibits In-Stent Coronary Intimal Proliferation in Renal Transplant Patients," American Heart Association, 2002, p. 2928.
Morice et al., "A Randomized Comparison of a Sirolimus-Eluting Stent With a Standard Stent for Coronary Revascularization," The New England Journal of Medicine, Jun. 6, 2012, p. 1773-1780, vol. 346, No. 23.
Muller-Leisse et al., "Effectiveness and Safety of Ultrasonic Atherosclerotic Plaque Ablation: In Vitro Investigation," CardioVascular and Interventional Radiology, 1993, p. 303-307, vol. 16.
Nair et al., "Regularized Autoregressive Analysis of Intravascular Ultrasound Backscatter: Improvement in Spatial Accuracy of Tissue Maps," IEEE Transactions on Ultrasonics, Apr. 2004, p. 420-431, vol. 51, No. 4.
Popma et al., "Percutaneous Coronary and Valvular Intervention," p. 1364-1405.
Resar et al., "Endoluminal Sealing of Vascular Wall Disruptions With Radiofrequency-Heated Balloon Angioplasty," Catheterization and Cardiovascular Diagnosis, 1993, p. 161-167, vol. 29.
Romer et al., "Histopathology of Human Coronary Atherosclerosis by Quantifying Its Chemical Composition With Raman Spectroscopy," Circulation, 1998, p. 878-885, vol. 97.
Schauerte et al., "Catheter Ablation of Cardiac Autonomic Nerves for Prevention of Vagal Atrial Fibrillation," Circulation, 2000, p. 2774-2780, vol. 102.
Scheller et al., "Intracoronary Paclitaxel Added to Contrast Media Inhibits In-Stent Restenosis of Porcine Coronary Arteries," American Heart Association, 2002, p. 2227.
Scheller et al., "Potential solutions to the current problem: coated balloon," EuroIntervention, 2008, p. C63-C66, vol. 4 (Supplement C).

(56) References Cited

OTHER PUBLICATIONS

Shaffer, "Scientific basis of laser energy," Clinics in Sports Medicine, 2002, p. 585-598, vol. 21.

Shmatukha et al., "MRI temperature mapping during thermal balloon angioplasty," Physics in Medicine and Biology, 2006, p. N163-N171, vol. 51.

Slager et al., "Vaporization of Atherosclerotic Plaques by Spark Erosion," J Am Coll Cardiol, 1985, p. 21-25.

Stiles et al., "Simulated Characterization of Atherosclerotic Lesions in the Coronary Arteries by Measurement of Bioimpedance," IEEE Transactions on Biomedical Engineering, Jul. 2003, p. 916-921, vol. 50, No. 7.

Suselbeck et al., "In vivo intravascular electric impedance spectroscopy using a new catheter with integrated microelectrodes," Basic Res Cardiol, 2005, p. 28-34, vol. 100.

Suselbeck et al., "Intravascular electric impedance spectroscopy of atherosclerotic lesions using a new impedance catheter system," Basic Res Cardiol, 2005, p. 446-452, vol. 100.

Tepe et al., "Local Delivery of Paclitaxel to Inhibit Restenosis during Angioplasty of the Leg," The New England Journal of Medicine, 2008, p. 689-699, vol. 358.

Brown et al., "Radiofrequency capacitive heaters: the effect of coupling medium resistivity on power absorption along a mouse leg" Phys Med Biol 1993, 381-12 (abstract).

Cardiovascular Technologies, Inc., "Heated Balloon Device Technology" [Presentation], 2007-2008, 11 pages total. Retrieved from: <<http://www.cvtechinc.com/pr/presoCVT Heated Balloon Tech.pdf>>.

Carrington, "Future of CVI: It's All About the Plaque." Diagnostic Imaging Special Edition Forum [online] [retrieved on Sep. 3, 2003] Retreived from the Internet:,http://dimag.com/specialedition/cardiacimg.shtml> 5 pages total.

Cimino, "Preventing Plaque Attack", [online] [retrieved on Sep. 3, 2003] Retrieved from the Internet: <http://Massh ig htech.com/displayarticledetai 1.ap?art id=52283&cat_id= 1 0>, 3 pages total.

Kaplan et al., "Healing after arterial dilatation with radiofrequency thermal and nonthermal balloon angioplasty systems," J Invest Surg. Jan.-Feb. 1993;6(1 ):33-52.

Kolata, "New Studies Question Value of Opening Arteries", New York Times [online] [retrieved on Jan. 25, 2005]. Retrieved from the Internet: <http:/lnytimes.com/2004/03/21 /health/21 HEAR.html?ei=5070&en=641 bc03214e&e04-1 0-2009 =11 067>, 5 pages total.

Konings M K, et al., "Development of an Intravascular Impedance Catheter for Detection of Fatty Lesions in Arteries," IEEE Transactions on Medical Imaging, vol. 51, No. 4, Apr. 2004.

Kurtz et al., "Lamellar Refractive Surgery with Scanned Intrastromal Picosecond and Femtosecond Laser Pulses in Animal Eyes", J Refract Surg, vol. 14, (Sep./Oct. 1998), pp. 541-548.

Lightlab Imaging Technology, "Advantages of OCT", [online] [retrieved on Sep. 3, 2003]. Retrieved from the Internet: <http:www.lightlabimaging.com/advantage.html> 2 pages total.

Lightlab Imaging Technology, "LightLab Imaging Starts US Cardiology Clinical Investigations", LightLab Company Press Release, [online] [retrieved on Sep. 3, 2003]. Retrieved from the Internet: <http://www.lighlabimaging.com/press/cardtrails.html> 2 pages total.

Lightlab Imaging Technology, "What is OCT?", [online] [retrieved on Sep. 3, 2003]. Retrieved from the Internet: <http:lightlabimaging.com/oct.html.> 2 pages total.

Lightlab Imaging Technology, "Why use OCT?", [online] [retrieved on Sep. 3, 2003]. Retrieved from the Internet: <http:lightlabimaging.com/whyoct.html> 2 pages total.

Lima et al., "Efficacy and Safety of Oral Sirolimus to Treat and Prevent In-Stent Restenosis: A Pilot Study Results", Abstract #2929, AHA (2002), 1 page total.

Lima et al., "Systemic Immunosuppression Inhibits In-Stent Coronary Intimal Proliferation in Renal Transplant Patients", Abstract #2928, AHA (2002), 1 page total.

MIT Techtalk, "Laser Catheter to Aid Coronary Surgery", Jan. 9, 1991 [online] [retrieved on Feb. 7, 2005]. Retrieved from the Internet: <http://web.mit.edu/newsoffice/tU1991/jan09/24037.html> 4 pages total.

Morice et al., "A Randomized Comparison of a Sirolimus-Eiuting Stent With a Standard Stent for Coronary Revascularization", N. Eng/J Med, vol. 346, No. 23, (Jun. 6, 2002), pp. 1773-1779.

Moller et al., "Effectiveness and Safety of Ultrasonic Atherosclerotic Plaque Ablation: In Vitro Investigation", CardioVas.Intervent. Radio/., (1993) 16: 303-307.

Nair A, et al., "Regularized Autoregressive Analysis of Intravascular Ultrasound Backscatter: Improvement in Spatial Accuracy of Tissue Maps," IEEE Transactions on Ultrasonics, Ferroelectrics, and Frequency Control, vol. 51 No. 4, Apr. 2004.

Popma et al., "Chapter 38—Percutaneous Coronary and Valvular Intervention", Heart Disease: A Textbook of Cardiovascular Medicine, 6th ed., (2001) W.B> Saunders Company, pp. 1364-1405.

Romer et al., "Histopathology of Human Coronary Atherosclerosis by Quantifying Its Chemical Composition with Raman Spectroscopy," Circulation 97:878-885 (1998).

Scheller, "Intracoronary Paclitaxel Added to Contrast Media Inhibits In-Stent Restenosis of Porcine Coronary Arteries", Abstract #2227, AHA (2002), 2 pages total.

Scheller et al., "Potential Solutions to the Current Problem: Coated Balloon," EuroIntervention, Aug. 2008; 4 Suppl C: C63-66.

Shaffer, "Scientific Basis of Laser Energy", Clin Sports Med 2002; 21 (4 ):585-598.

Shmatukha A V, et al., "MRI temperature mapping during thermal balloon angioplasty," Phys Med Bioi 51, (2006) N163-N171.

Slager et al., "Vaporization of Atherosclerotic Placques by Spark Erosion," JAm Coli Cardiol, vol. 5 (Jun. 1985) pp. 1382-1386.

Stiles et al., "Simulated Charactization of Atherosclerotic Lesions in the Coronary Arteries by Measurement of Bioimpedance," IEEE Transactions on Biomedical Engineering, (Jul. 2003), 5(4):916-921.

Soselbeck et al. "Intravascular electric impedance spectroscopy of atherosclerotic lesions using a new impedance system", Basic Res Cardiol (2005) 100:446-452.

Suselbeck T, et al., "In vivo intravascular electrical impedance spectroscopy using a new catheter with integrated microelectrodes," Basic Res Cardiol 100:28-34 (2005).

Tepe et al., "Local Delivery of Paclitaxel to Inhibit Restenosis During Angioplasty of the 41 Leg," N Engl J Med, Feb. 14, 2008; 358(7): 689-699; retrieved from the Internet: <<http://content.nejm.org/cgi/reprint/358/7/689.pdf>>.

Van Den Berg, "Light Echoes Image the Human Body", OLE, Oct. 2001, pp. 35-37.

Volcano Therapeutics, "Product—Functional Measurement", [online] [retrieved on Mar. 9, 2003]. Retrieved from the Internet: <http://www.volcanotherapeutics.com/pages/products/functional_measurement-us.html> 2 pages total.

CardioVascular Technologies Inc., "Heated Balloon Device Technology," 11 pages, 2008.

Strategic Business Development, Inc., "Thermal and Disruptive Angioplasty: A Physician's Guide," 8 pages, 1990.

Zhang et al., "Non-contact Radio-Frequency Ablation for Obtaining Deeper Lesions," IEEE Transaction on Biomedical Engineering, vol. 50, No. 2, 6 pages, Feb. 2003.

Lazebnik et al., "Tissue Strain Analytics Virtual Touch Tissue Imaging and Qualification," Siemens Whitepaper, Oct. 2008, 7 pages.

Han et al., "Third-Generation Cryosurgery for Primary and Recurrent Prostate Caner," BJU International, vol. 93, pp. 14-18.

Zhou et al., "Mechanism Research of Cryoanalgesia," Forefront Publishing Group, 1995.

Florete, "Cryoblative Procedure for Back Pain," Jacksonville Medicine, Oct. 1998, 10 pages.

Stevenson, "Irrigated RF Ablation: Power Titration and Fluid Management for Optimal Safety Efficacy," 2005, 4 pages.

Giliatt et al., "The Cause of Nerve Damage in Acute Compression," Trans Am Neurol Assoc, 1974: 99; 71-4.

Omura et al., "A Mild Acute Compression Induces Neurapraxia in Rat Sciatic Nerve," The International Journal of Neuroscience, vol. 114 (12), pp. 1561-1572.

(56) References Cited

OTHER PUBLICATIONS

Baun, "Interaction with Soft Tissue," Principles of General & Vascular Sonography, Chapter 2, pp. 23-24, Before Mar. 2012.
Blue Cross Blue Shield Medicaly Policy, "Surgery Section—MRI-Guided Focused Ultrasound (MRgFUS) for the Treatment of Uterine Fibroids and Other Tumors," 2005, 5 pages.
Gentry et al., "Combines 3D Intracardiac Echo and Ultrasound Ablation," Medical Imaging 2003: Ultrasonic and Signal Processing, vol. 5035, 2003, pp. 166-173.
Lafon et al., "Optmizing the Shape of Ultrasound Transducers for Interstitial Thermal Ablations," MEd Phys. Mar. 2002; 29(3): 290-7 (abstract only).
G. Ter Haar, "Ultrasound Focal Beam Surgery," Ultrasound in Med. & Biol., 1995, vol. 21, No. 9, pp. 1089-1100.
Seip et al., "Transurethral High Intensity Focused Ultrasound: Catheter Based Prototypes and Experimental Results," IEEE Ultrasonics Symposium Proceeding, 2000, 4 pages.
Toytman et al., "Tissue Dissection with Ultrafast Laser Using Extended and Multiple Foci," SPIE Proceeding, Optical Interactions with Tissues and Cells XXI, vol. 7562, 2010, 10 pages.
Zhoue et al., "Non-Thermal Ablation of Rabbit Liver VX2 Tumore by Pulsed High Intensity Focused Ultrasound Contrast Agent: Pathological Characteristics," World Journal of Gastroenterology, vol. 14(43), Nov. 21, 2008, pp. 6743-6747.
Dahm et al, "Relation of Degree of Laser Debulking of In-Stent Restenosis as a Predictor of Restenosis Rate", Am J Cardiol, 2002; 90(1): 68-70.
De Korte C L. et al., "Characterization of Placque Components with Intravascular Ultrasound Elastography in Human Femoral and Coronary Arteries In Vitro," Circulation 2000;102:617-623.
Durney C., et al., Radiofrequency Radiation Dosimetry Handbook (with table of contents), Oct. 1986, 4th ed., 7 pages, Armstrong Laboratory (AFMC) Occupational and Environmental Health Directorate Radiofrequency Radiation Division, USAF School of Aerospace Medicine, Aerospace Medical Division (AFSC), Brooks Air Force Base, http://www.brooks.af.mii/AFRLIHED/hedr/reports/handbook/home.htm.
Fournier-Desseux et al. "Assessment of 1-lead and 2-lead electrode patterns in electrical impedance endotomography", Physiol. Meas. (2005) 26:337-349.
Fujimori et al., "Significant Prevention of In-Stent Restenosis by Evans Blue in Patients with Acute Myocardial Infarction", Abstract #2925, AHA (2002), 1 page total.
Fujita, "Sarpogrelate, An Antagonist of 5-HTza Receptor Treatment Reduces Restenosis After Coronary Stenting", Abstract #2927, AHA (2002), 1 page total.
Gabriel C, et al., Compilation of the Dielectric Properties of Body Tissues at RF and Microwave Frequencies (with table of contents), Jun. 1996, 17 pages, Armstrong Laboratory (AFMC) Occupational and Environmental Health Directorate Radiofrequency Radiation Division, USAF School of Aerospace Medicine, Aerospace Medical Division (AFSC), Brooks Air Force Base, http://www.brooks.af.mii/AFRLIHED/hedr/reports/dielectric/ReporUReport.html.
Gregory et al., "Liquid Core Light Guide for Laser Angioplasty", Journal of Quantum Electronics, vol. 26, No. 12, (Dec. 1990), pp. 2289-2296.
Intraluminal, Product description [online] [retrieved on Sep. 3, 2003] Retrieved from the Internet: http://www.intraluminal.com/products/inde04-1 0-2009.html> 1 page total.
US 8,398,630, 03/2013, Demarais et al. (withdrawn)

* cited by examiner

SELECTIVE DRUG DELIVERY IN A LUMEN

CROSS-REFERENCES TO RELATED APPLICATIONS

This application is a continuation of U.S. patent application Ser. No. 12/616,720 filed Nov. 11, 2009, now U.S. Pat. No. 8,396,548; which claims the benefit under 35 USC 119(e) of U.S. Provisional Application No. 61/114,958 filed Nov. 14, 2008; the full disclosures of which are incorporated herein by reference in their entirety.

BACKGROUND OF THE INVENTION

The present invention is generally related to medical devices, systems, and methods. In particular, the invention provides methods and systems for selective drug delivery to body tissue disposed about a lumen using a catheter-based treatment system.

Physicians use catheters to gain access to and repair interior tissues of the body, particularly within the lumens of the body such as blood vessels. For example, balloon angioplasty and other catheters often are used to open arteries that have been narrowed due to atherosclerotic disease. Balloon angioplasty is often effective at opening an occluded blood vessel, but the trauma associated with balloon dilation can impose significant injury, so that the benefits of balloon dilation may be limited in time.

Stenting, in conjunction with balloon dilation, is often the preferred treatment for atherosclerosis. In stenting, a collapsed metal framework is mounted on a balloon catheter which is introduced into the body. The stent is manipulated into the site of occlusion and expanded in place by the dilation of the underlying balloon. Stenting has gained widespread acceptance, and produces generally acceptable results in many cases. Along with treatment of blood vessels (particularly the coronary arteries), stents can also be used in treating many other tubular obstructions within the body, such as for treatment of reproductive, gastrointestinal, and pulmonary obstructions. Restenosis or a subsequent narrowing of the body lumen after stenting has occurred in a significant number of cases.

A variety of modified restenosis treatments or restenosis-inhibiting treatment modalities have also been proposed, including intravascular radiation, cryogenic treatments, ultrasound energy, and the like, often in combination with balloon angioplasty and/or stenting. While these and different approaches show varying degrees of promise for decreasing the subsequent degradation in blood flow following angioplasty and stenting, the trauma initially imposed on the tissues by angioplasty remains problematic.

A number of alternatives to stenting and balloon angioplasty have been proposed to open stenosed arteries. For example, a wide variety of atherectomy devices and techniques have been disclosed and attempted. Despite the disadvantages and limitations of angioplasty and stenting, atherectomy has not gained the widespread use and success rates of dilation-based approaches. More recently, still further disadvantages of dilation have come to light. These include the existence of vulnerable plaque, which can rupture and release materials that may cause myocardial infarction or heart attack.

More recently, drug coated stents (such as Johnson and Johnson's Cypher stent, the associated drug comprising Sirolimus) have demonstrated a markedly reduced restenosis rate, and others are developing and commercializing alternative drug eluting stents. While drug eluting stents appear to offer significant promise for treatment of atherosclerosis in many patients, there remain many cases where stents either cannot be used or present significant disadvantages. Generally, stenting leaves an implant in the body. Such implants can present risks, including mechanical fatigue, corrosion, thrombus formation, and the like, particularly when removal of the implant is difficult and involves invasive surgery. Stenting may have additional disadvantages for treating diffuse artery disease, for treating bifurcations, for treating areas of the body susceptible to crush, and for treating arteries subject to torsion, elongation, and shortening.

In light of the above, it would be advantageous to provide methods and systems for selective fluid delivery to artery tissue that avoids the drawbacks associated with drug eluding stents and the devices described above.

BRIEF SUMMARY OF THE INVENTION

The present invention generally provides devices, systems, and methods for selective drug or fluid delivery to a body tissue being disposed about a lumen.

In a first aspect, the invention comprises a system for selective drug delivery to a body tissue being disposed about a lumen. The system includes an elongated flexible catheter body having a proximal end and a distal end with a radially expandable balloon near the distal end of the catheter body. An energy delivery surface disposed about the expandable balloon and a thermally changeable drug coating is coupled to the balloon, the energy delivery surface and the thermally changeable coating being oriented to be urged against the body tissue when the expandable balloon expands. An energy source is operatively coupled to the energy delivery surface configured to energize the energy delivery surface to heat and liquefy the thermally changeable coating to release the drug to the body tissue.

In another aspect, the invention comprises a method for selective drug delivery in a lumen. The method includes engaging a body tissue disposed about the lumen with an energy delivery surface and a thermally changeable coating having a releasable drug disposed on a radially expandable balloon near a distal end of a catheter when the expandable balloon expands, selectively energizing the energy delivery surface to heat and liquefy portions of the thermally changeable drug coating, and releasing a drug from the coating into the body tissue.

In many embodiments, the energy delivery surface comprises a plurality of electrodes, the energy source operatively coupled to the plurality of electrodes so as to selectively energize electrode pairs to heat and liquefy portions of the thermally changeable coating between the electrode pairs to release the drug to the body tissue. In many embodiments the body tissue of the lumen includes a diseased portion and select electrode pairs are energized to selectively heat the thermally changeable coating proximate the diseased portion.

In many embodiments, the energy delivery surface comprises a plurality of electrodes disposed about the expandable balloon so as to define a plurality of remodeling zones in the tissue when the balloon is expanded within the lumen, the electrodes are radially coupled with the tissue, and energy is transmitted between the electrodes and the tissue.

In many embodiments, further comprising a tissue analyzer configured to characterize the body tissue.

In many embodiments, the energy delivery surface is energized to heat the thermally changeable coating to release the drug in responses to the characterized body tissue.

In many embodiments, the body tissue of the lumen includes a diseased portion and select electrode pairs are energized to selectively heat the thermally changeable coating proximate the diseased portion.

In many embodiments, the energy delivery surface is energized to heat the body tissue in combination with the drug delivery.

In many embodiments, the thermally changeable drug coating includes more than one drug.

In many embodiments, the drug is selected from at least one of, a therapeutic fluid, an anesthetic drug, a therapeutic drug, a small molecule, a gene therapeutic compound, an anti-thrombolytic agent, a lubricant (to allow higher temperatures without sticking), an electrically conductive compound to lower the impedance at the electrode, an electrically insulating compound to prevent treatment to tissue that does not need treatment, an electrically conductive compound that is intended to migrate through the endothelial layers of tissue to carry energy to the interstitial layers, or a combination of the above.

In another aspect, the invention comprises a catheter system for drug delivery to a body tissue being disposed about a lumen. The system includes an elongated flexible catheter body having a proximal end and a distal end, a radially expandable balloon near the distal end of the catheter body, and an energy delivery surface disposed about the expandable balloon. A plurality of biomolecules having a thermally releasable drug portion and an inert portion covalently bound to the balloon and an energy source operatively coupled to the energy delivery surface so as to heat the biomolecules to release the drug portion to the body tissue.

In another aspect, the invention comprises a method for fluid delivery in a lumen. The method includes engaging a body tissue disposed about the lumen with an energy delivery surface and a plurality of biomolecules having a thermally releasable drug portion and an inert portion covalently bound to the balloon near a distal end of a catheter when the expandable balloon expands, energizing the energy delivery surface to heat the biomolecules, and releasing the drug portion from the biomolecules into the body tissue.

In many embodiments, the energy delivery surface comprises a plurality of electrodes, the energy source operatively coupled to the plurality of electrodes so as to selectively energize electrode pairs to heat the biomolecules between the electrode pairs to release the drug portion to the body tissue.

In many embodiments, the body tissue of the lumen includes a diseased portion and select electrode pairs are energized to selectively heat the biomolecules proximate to the diseased portion.

In many embodiments, the energy delivery surface and biomolecules are oriented to be urged against the body tissue when the expandable balloon expands.

In many embodiments, further comprising a tissue analyzer configured to characterize the body tissue and the energy delivery surface is energized to heat the biomolecules to release the drug portion in responses to the characterized body tissue.

In many embodiments, the energy delivery surface is further energized to heat the body tissue in combination with the drug delivery.

In many embodiments, the biomolecules include more than one releasable drug.

In many embodiments, the drug portion is selected from at least one of, a therapeutic fluid, an anesthetic drug, a therapeutic drug, a small molecule, a gene therapeutic compound, an anti-thrombolytic agent, a lubricant (to allow higher temperatures without sticking), an electrically conductive compound to lower the impedance at the electrode, an electrically insulating compound to prevent treatment to tissue that does not need treatment, an electrically conductive compound that is intended to migrate through the endothelial layers of tissue to carry energy to the interstitial layers, or a combination of the above.

In another aspect, the invention comprises a catheter system for selective fluid delivery to a body tissue being disposed about a lumen. The system includes an elongated flexible catheter body having a proximal end and a distal end, a radially expandable structure near the distal end of the catheter body, a plurality of fluid delivery channels oriented to be urged against the body tissue when the expandable structure expands, the fluid delivery channels being initially blocked with a thermally changeable material, and an energy source connector operatively coupled to the fluid delivery channels so as to heat and liquefy the thermally changeable material to selectively open one or more of the fluid delivery channels for fluid release.

In another aspect, the invention comprises a catheter system for selective fluid delivery to a body tissue being disposed about a lumen. The system includes an elongated flexible catheter body having a proximal end and a distal end, a radially expandable structure near the distal end of the catheter body, a plurality of fluid delivery channels oriented to be urged against the body tissue of the lumen when the expandable structure expands, the fluid delivery channels being initially closed, and a plurality of micro-electromechanical systems (MEMS) coupled to the fluid delivery channels to selectively open one or more fluid delivery channels and release a fluid in the lumen.

In another aspect, the invention comprises a method for selective fluid delivery in a lumen. The method includes engaging a body tissue disposed about the lumen with a plurality of fluid delivery channels on a radially expandable structure near a distal end of a catheter when the expandable structure expands, selectively opening one or more fluid delivery channels, and releasing a fluid from the select fluid delivery channels into the lumen.

In many embodiments, the plurality of fluid delivery channels protrude from the expandable structure to penetrate the body tissue of the lumen.

In many embodiments, further comprising a tissue analyzer configured to characterize the body tissue to identify body tissue to be treated and selectively opening or closing one or more fluid delivery channels in responses to the characterized body tissue to treat the identified body tissue.

In many embodiments, the fluid delivery channels can be selectively energized to selectively open one or more fluid delivery channels in responses to the characterized body tissue.

In many embodiments, the radially expandable structure comprises a balloon and the fluid delivery channels are mounted on a circumference of the balloon.

In many embodiments, the radially expandable structure comprises an expandable basket and the fluid delivery channels are mounted on a circumference of the basket.

In many embodiments, the body tissue of the lumen includes a diseased portion and select electrodes are energized to selectively open one or more fluid delivery channels proximate the diseased portion.

In many embodiments, select electrodes are energized to heat the body tissue in conjunction with the release of the fluid in the lumen.

In many embodiments, selectively opening one or more fluid delivery channels comprises selectively energizing electrodes coupled to the select fluid delivery channels to heat the select fluid delivery channels to liquefy a thermal material initially closing the fluid delivery channel.

In many embodiments, the fluid is selected from at least one of, ceramide, suramin, rapamycin, paclitaxel, sirolimus, zotarolimus, everolimus, a therapeutic fluid, an anesthetic drug, a therapeutic drug, a small molecule, a gene therapeutic compound, an anti-thrombolytic agent, a lubricant (to allow higher temperatures without sticking), an electrically conductive compound to lower the impedance at an electrode, an electrically insulating compound to prevent treatment to tissue that does not need treatment, an electrically conductive compound that is intended to migrate through the endothelial layers of tissue to carry energy to the interstitial layers, or a combination of the above.

In yet another aspect, the invention comprises a method for selective fluid delivery in a lumen. The method includes engaging a body tissue disposed about the lumen with a plurality of fluid delivery channels on a radially expandable structure near a distal end of a catheter when the expandable structure expands, the balloon material is a membrane of a fixed pore size, and adding energy or heat to the fluid adjacent to the balloon surface allows the specific molecules to be passed through the membrane at the specific region for the specific time by virtue of the energy/heat source being switched on or off.

DETAILED DESCRIPTION OF THE INVENTION

Figure 1:
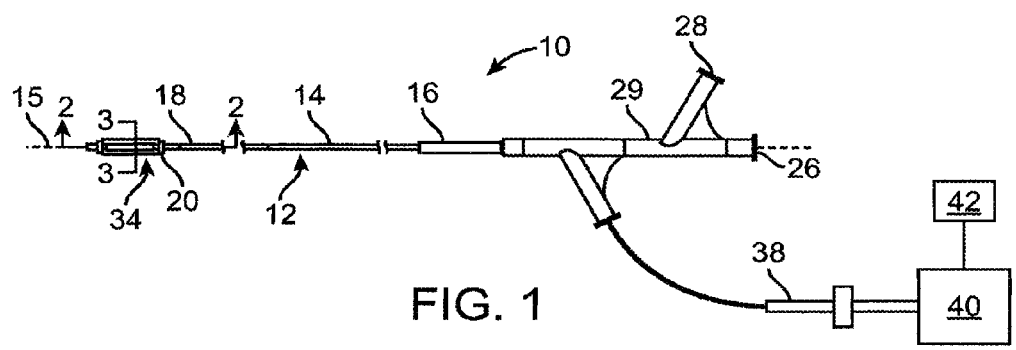
FIG. 1 schematically illustrates one embodiment of a catheter system having a coating for selective drug delivery to a body tissue being disposed about a lumen.

Many therapies have been developed to replace or improve upon traditional balloon angioplasty and stents. The alternative devices described in the BACKGROUND OF THE INVENTION either cut, ablate, or vaporize diseased tissue in an artery. For example, laser devices vaporize plaque and flush it downstream. Atherectomy devices excise plaque and suck it out of the body. Cutting balloons incise the artery wall, damaging the tissue. Even a simple angioplasty balloon does trauma to the tissue. It would be advantageous to provide treatments to body tissue that do not cut, ablate, or vaporize.

The present invention discloses systems and methods for selective delivery of a fluid to body tissue in a lumen, in particular, selective drug delivery in a lumen. Selective delivery may also control when and where the drug is delivered, and the amount of drug delivered.

While the disclosure focuses on drug delivery, such as, ceramide, suramin, rapamycin, paclitaxel, sirolimus, zotarolimus, everolimus, a drug (anesthetic or therapeutic), many other suitable fluids may be also be delivered to body tissue, for example, a therapeutic fluid, a small molecule, a gene therapeutic compound, an anti-thrombolytic agent, a lubricant (to allow higher temperatures without sticking), an electrically conductive compound to lower the impedance at the electrode, an electrically insulating compound to prevent treatment to tissue that does not need treatment, an electrically conductive compound that is intended to migrate through the endothelial layers of tissue to carry energy to the interstitial layers, or a combination of the above.

In some embodiments of the present invention, a drug is incorporated into a coating on a balloon catheter that is thermally released once inside the lumen to selectively treat the tissue. In other embodiments, a fluid or drug may be delivered through fluid delivery channels in a catheter system to selectively treat the tissue. In still other embodiments, multiple fluids or drugs may be delivered as part of a coating, through the fluid delivery channels, by thermal osmosis through a membrane, or any combination thereof. In some embodiments the drug may be delivered at one tissue site, while other embodiments portions of the drug to different sites.

Some embodiments of the present invention use heating to release the drug coating. Other embodiments combine fluid or drug delivery with heating of the tissue before, during or after delivery to the tissue. Devices for heating artery tissue using RF, ultrasound, microwave and laser energies have been disclosed in co-pending U.S. patent application Ser. Nos. 11/975,474, 11/975,383, 11/122,263 and U.S. Provisional Application No. 61/099,155, the full disclosures of which are incorporated herein by reference.

Drug Delivery During an Angioplasty Procedure

Some embodiments of the present invention provide systems and methods for drug delivery in a lumen in combination with heating during an angioplasty procedure. While drugs are disclosed, proteins, cells and/or molecules may also be delivered (discussed below). The angioplasty procedure itself is the procedure that will open the lumen. The heating will cause softening and shrinking of a lesion, enabling the plaque to reshape easily around the balloon while avoiding stretching of the vessel thus avoiding injury to the vessel. The drug will be released during the angioplasty procedure and the heating process. Drug delivery treatment during an angioplasty procedure will be a combination of:

Pressure—due to the balloon in order to open the lumen. The pressure may be standard angioplasty dilation pressures of 10-16 atmospheres or may be more gentle dilation pressures of 6 atmospheres or less, and possibly as low as 1 to 2 atmospheres.

Heating—due to the RF energy in order to soften and shrink the lesion. Heating may also have other benefits related to the drug or drug delivery (discussed below).

Drug/Protein/Cell/Molecule—which will be released during the procedure.

The Drug/Molecule/Protein/Cell element can be built of one component, or in combination of others such as:

1. Drugs: any molecule which will enable prevention or reduction of smooth muscle cell (SMC) proliferation and/or migration from the media to the intima, for example: ceramide, suramin, rapamycin and paclitaxel. The heating of the tissue may have a key role in helping deliver the drug into the lesion or tissue, and deeper into the media.

2. Proteins: proteins such as anti-inflammatory proteins, antibodies and other kinds of proteins which will enable the reduction and healing of the inflammation inside the lesion, or enable prevention or reduction of SMC proliferation and migration. We can also use protein that will induce cell apoptosis or oncosis. The heating may have a key role in activating these proteins during the treatment, and if heated quickly during the procedure, enabling the maximum time exposure of the tissue to the proteins. In order to make sure that the proteins will be activated during the procedure, one should take into account the half-life of a protein. The half-life of a protein is the time it takes before any half of the protein pool for that particular protein is left. for human proteins, it ranges from minutes to 80 hours. In order to use proteins eluting balloon, the balloon needs to be maintained in lower temperature (<0° C.), so the proteins won't be ruined and destroyed. Several of the proteins that may be combined to a molecule named Adenosine-5'-triphosphate (ATP). ATP is a multifunctional nucleotide that is important as a "molecular currency" of intracellular energy transfer. In one example, the balloon is covered with the protein and the electrodes are covered with ATP (or the opposite) and the protein will be released with the balloon inflation, and the ATP will be released when the energy will be emitted from the electrodes (or the opposite).

3. Cells: coating the balloon with cells such as endothelium, or any other type of cell which can migrate to the lesion during the procedure, where they will release proteins or antibodies to heal the inflammation or prevent SMC proliferation and migration. The heat in this case is also to activate the cells during the procedure.

4. Molecules or proteins that can be attached or become activated when attached to heat shock proteins (HSP). HSP are a group of proteins whose expression is increased when the cells are exposed to elevated temperatures or other stress. For example, HSP27 functions in smooth muscle cells (SMC) migration. In this case the RF energy and the heating will result in elevation of HSP27 inside the SMC, so we can use any drug/molecule or protein directly to the SMC by using anti-HSP27 antibody. The concept is to use the heat and the outcomes of the heat in order to use other molecules or proteins to bind, degrade, inhibit or activate other proteins or cells in the lesion and in the media, in order to prevent restenosis.

Drug Delivery Coatings

FIG. 1 shows one embodiment of a catheter system 10 having a releasable coating for selective drug delivery to a body tissue being disposed about a lumen. The catheter system 10 includes a balloon catheter 12 having a catheter body 14 with a proximal end 16 and a distal end 18. Catheter body 14 is flexible and defines a catheter axis 15, and may include one or more lumens, such as a guidewire lumen 22 and an inflation lumen 24. Catheter 12 includes an inflatable balloon 20 adjacent distal end 18 and a housing 29 adjacent proximal end 16. Housing 29 includes a first connector 26 in communication with guidewire lumen 22 and a second connector 28 in fluid communication with inflation lumen 24. Inflation lumen 24 extends between balloon 20 and second connector 28. Both first and second connectors 26, 28 may optionally comprise a standard connector, such as a Luer-Loc™ connector. A distal tip may include an integral tip valve to allow passage of guidewires, and the like.

Housing 29 also accommodates an electrical connector 38. Connector 38 includes a plurality of electrical connections, each electrically coupled to electrodes 34 via conductors 36. This allows electrodes 34 to be easily energized, the electrodes often being energized by a controller 40 and power source 42, such as RF energy. In one embodiment, electrical connector 38 is coupled to an RF generator via a controller 40, with controller 40 allowing energy to be selectively directed to electrodes 34. While RF energy is disclosed, other suitable energy sources may be used, such as microwave energy, ultrasound energy, or laser energy, each having energy delivery portions configured to deliver the desired energy. See co-pending U.S. Provisional Application No. 61/099,155, the full disclosures of which are incorporated herein by reference.

In some embodiments, controller 40 may include a processor or be coupled to a processor to control or record treatment. The processor will typically comprise computer hardware and/or software, often including one or more programmable processor unit running machine readable program instructions or code for implementing some or all of one or more of the methods described herein. The code will often be embodied in a tangible media such as a memory (optionally a read only memory, a random access memory, a non-volatile memory, or the like) and/or a recording media (such as a floppy disk, a hard drive, a CD, a DVD, a non-volatile solid-state memory card, or the like). The code and/or associated data and signals may also be transmitted to or from the processor via a network connection (such as a wireless network, an Ethernet, an internet, an intranet, or the like), and some or all of the code may also be transmitted between components of catheter system 10 and within processor via one or more bus, and appropriate standard or proprietary communications cards, connectors, cables, and the like will often be included in the processor. Processor will often be configured to perform the calculations and signal transmission steps described herein at least in part by programming the processor with the software code, which may be written as a single program, a series of separate subroutines or related programs, or the like. The processor may comprise standard or proprietary digital and/or analog signal processing hardware, software, and/or firmware, and will typically have sufficient processing power to perform the calculations described herein during treatment of the patient, the processor optionally comprising a personal computer, a notebook computer, a tablet computer, a proprietary processing unit, or a combination thereof. Standard or proprietary input devices (such as a mouse, keyboard, touchscreen, joystick, etc.) and output devices (such as a printer, speakers, display, etc.) associated with modern computer systems may also be included, and processors having a plurality of processing units (or even separate computers) may be employed in a wide range of centralized or distributed data processing architectures.

Figure 2:
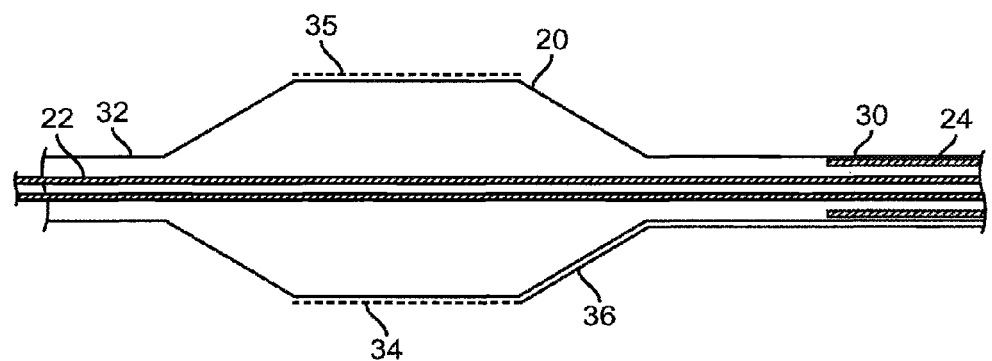
FIG. 2 schematically illustrates one embodiment of an inflatable balloon for use in the catheter system of FIG. 1.

Balloon 20 is illustrated in more detail in FIG. 2. Balloon 20 generally includes a proximal portion 30 coupled to inflation lumen 24 and a distal portion 32 coupled to guidewire lumen 22. Balloon 20 expands radially when inflated with a fluid or a gas. In some embodiments, the fluid or gas may be non-conductive and/or cooled. In some embodiments, balloon 20 may be a low pressure balloon pressurized to contact the artery tissue. In other embodiments, balloon 20 is an angioplasty balloon capable of higher pressure to both heat the artery tissue and expand the artery lumen. Balloon 20 may comprise a compliant or non-compliant balloon having helical folds to facilitate reconfiguring the balloon from a radially expanded, inflated configuration to a low profile configuration, particularly for removal after use.

Electrodes 34 are mounted on a surface of balloon 20, with associated conductors 36 extending proximally from the electrodes. Electrodes 34 may be arranged in many different patterns or arrays on balloon 20. The system may be used for monopolar or bipolar application of energy. For delivery of bipolar energy, adjacent electrodes are axially offset to allow bipolar energy to be directed between adjacent circumferential (axially offset) electrodes. In other embodiments, electrodes may be arranged in bands around the balloon to allow bipolar energy to be directed between adjacent distal and proximal electrodes.

Figure 3A:
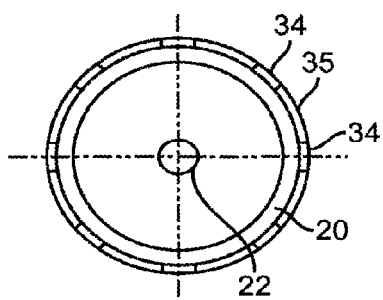
FIG. 3A schematically illustrates a cross-sectional view and 3B is an enlarged view of the balloon of FIG. 2.
Figure 3B:
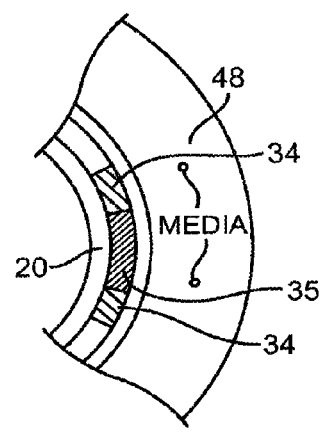

A coating 35 is coupled to the balloon 20 and positioned between electrodes 34, such as shown in FIGS. 3A and 3B. Coating 35 includes a fluid or drug to be delivered to the targeted tissue. It is envisioned that the coating will be thermally activated and configured to be released from the balloon surface at a temperature above body temperature (greater than 37 C). The idea is to have the energy delivery or heat, change the phase of a coating compound from a solid to a liquid, and releases the drug. This temperature increase involves activating electrodes 34 using RF energy. As the energy is increased, the coating 35 between the electrodes 34 is heated and released thermally to the local tissue 48. Coating 35 is durable or flexible such that it can be folded with the balloon 20 without separation or delamination. This mechanism could release small or large molecular drug or pharma product. The drug could be in a solid gel form.

Figure 4A:
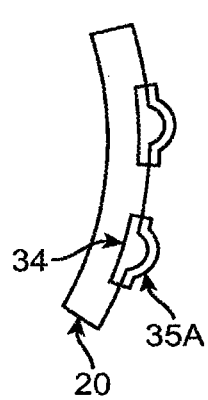
FIGS. 4A and 4B schematically illustrates coatings covering the electrodes.
Figure 4B:
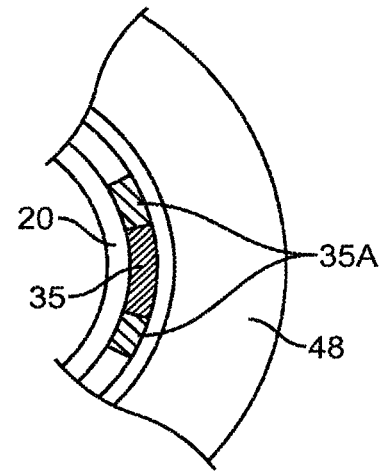

In some embodiments, a second coating 35A may be used to cover electrodes 34, such as shown in FIG. 4A. Second coating 35A may be an insulating coating on the electrodes 34. The second coating 35A would be used when treating inside a metallic object in the lumen, such as a stent, because if the electrodes 34 come in contact with metal, they may short and the treatment will end. If the electrodes 34 are coated with a material with electrical properties such that the electrodes can not be shorted with metallic objects, the treatment can continue even when in contact with metal objects. This would allow catheter system 10 to treat inside objects like stents. Second coating 35A may also act to insulate electrodes 34 from tissue 48, shown in FIG. 4B, which stops/prohibits energy flow through tissue 48 and sends the energy through coating 35, heating only the coating 35 between the electrodes 34, releasing the drug to the tissue 48. The second coating 35A may also include a different drug than coating 35.

Many types of drugs may be included in the coatings. For example, the coating may include drugs currently used in drug eluding stents, such as sirolimus (used in the Cypher™ stent), paclitaxel (used in the Taxus™ stent), zotarolimus (used in the Endeavour™ stent) and everolimus (used in the Xience V™ stent).

Some embodiments of the present invention may include aptamers 52 coated to the balloon 20 using a substrate that breaks down readily when heated, such as when the RF energy source is activated. Aptamers can be engineered to bind very specifically to various molecular targets such as small molecules, proteins, nucleic acids, and even cells, tissues and organisms. The aptamers 52 could be synthesized to bind 54 with desired tissue 48 to be treated, such as plaque, within the lumen or artery.

Figure 5:
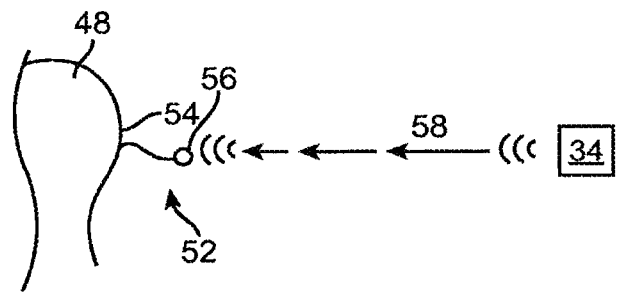
FIG. 5 schematically illustrates the used of aptamers in treating tissue.

While the catheter system 10 is not powered and the balloon 20 deflated, the coating 35 with aptamers 52 would remain on the balloon 20. Once the balloon 20 is inflated and the energy unit turned on, the coating is released and the aptamers 52 bind to the desired tissue, such as shown in FIG. 5. In some embodiments, aptamers 52 would be conjugated to a microscopic bead 56 that is highly receptive to the energy 58, such as RF energy, emitted by the catheter system 10. The beads 56 convert the RF energy to thermal energy directly and only to the tissue that the aptamers 52 is in contact with.

Aptamers are nucleic acids that bind to the surface of molecules in much the same way as antibodies. One importance difference between aptamers and antibodies is that aptamers can be produced by chemical synthesis whereas antibodies are produced biologically, first animals, then in culture or an expression system. Another important difference is that aptamers are very stable and not sensitive to their surrounding environment, including temperature.

In some embodiments, coating 35 may include a chemical solvent that has plaque softening properties. Ether, chloroform, benzene, and acetone are known to be lipid solvents. Furthermore, amino acids, proteins, carbohydrates, and nucleic acids are largely insoluble in these solvents. If the solvent is used in conjunction with tissue heating, the tissue treatment may require less energy over a shorter time period, lessening the chance of damage to healthy tissue. If the tissue includes calcium deposits, the same process used to deliver lipid solvents to plaque could be used to deliver calcium solvents to calcification sites. Calcium is highly soluble in a variety of organic solvents. In both cases, the solvent would be coupled to the surface of the balloon with a coating that would break down either with the application of heat or RF energy, or as the balloon is inflated.

In some embodiments, the coating may incorporate more than one drug, agent, or fluid listed herein within the coating, each having different phase change temperatures. For example, an anesthetic could be administered at a lower melting temperature prior to a specific treatment of higher temperature where there may be a nerve in the general location. Is some embodiments, two coatings of differing material may be used, such as by layering. For example, a first layer may include a first drug that attaches to the target tissue and act as a receptor to a second drug in a second layer. In some embodiments the coating is non-conductive to reduce or eliminate electrical shorts between electrodes.

In some embodiments, tissue signature could be used to identify treatment regions with the use of impedance measurements. Impedance measurements utilizing the radially spaced electrodes 34 within a lumen can be used to analyze tissue. Impedance measurements between pairs of adjacent electrodes (and/or between pairs of separated electrodes), may differ when the current path passes through diseased tissue, and when it passes through healthy tissues of the luminal wall. Hence, impedance measurements between the electrodes on either side of diseased tissue may indicate a lesion, while measurements between other pairs of adjacent electrodes indicate healthy tissue. Other characterization, such as intravascular ultrasound, optical coherence tomography, or the like may be used to identify regions to be treated.

Some embodiments described herein may be used to treat atherosclerotic disease by selective drug delivery in combination with "gentle heating" utilizing the "Q10 Rule" to further enhance the fluid or drug treatment. Under the Q10 Rule, it is well known that rates of biochemical reactions usually double when temperature is increased by 10° C.

Figure 6:
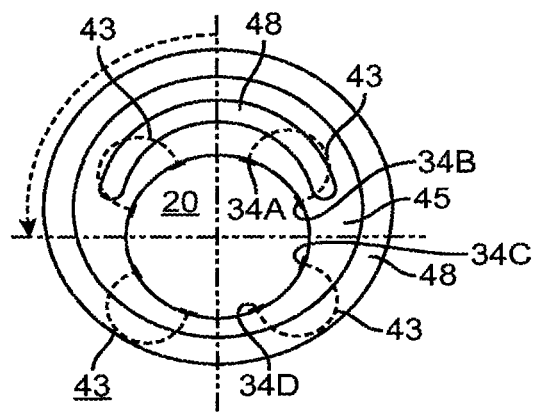
FIG. 6 schematically illustrates placement of electrode pairs for use in bipolar energy treatment before, during, or after drug delivery.

As shown in FIG. 6, electrodes 34 are positioned circumferentially around the balloon 20. RF energy 43 is directed to electrodes adjacent pairs of electrodes 34A and 34C, or 34A and 34D, or any combination of 34A-34D, treating both the healthy tissue 45 and atherosclerotic material 48 within lumen 50. This arrangement creates an energy path 43 through the tissue that delivers energy or heat ("tissue remodeling energy") in particular treatment zones or segments to the artery tissue between the electrode pairs ("remodeling zones") having a volume between the electrode pairs at a specific depth. Using different combinations of electrode pairs may reduce or eliminate gaps between the remodeling zones by using overlapping pairs. Using electrode pairs with bipolar energy may avoid some potential issues of the monopolar approach. Diseased artery tissue 48 has a higher electrical resistivity than healthy artery tissue. By using pairs of electrodes 34A, 34B in a bipolar system, tissue remodeling energy will go through the healthy tissue, diseased tissue, or a combination of both healthy and diseased tissues between the electrode pairs in the remodeling zones. Any number of electrode pairs may be used in different patterns or arrays to create a number of remodeling zones. The controller may apply either constant power, constant current, or constant voltage, whichever has the most advantage.

The controller 40 may energize the electrodes with about 0.25 to 5 Watts average power for 1 to 180 seconds, or with about 4 to 45 Joules. Higher energy treatments are done at lower powers and longer durations, such as 0.5 Watts for 90 seconds or 0.25 Watts for 180 seconds. Most treatments in the 2 to 4 Watt range are performed in 1 to 4 seconds. Using a wider electrode spacing, it would be appropriate to scale up the power and duration of the treatment, in which case the average power could be higher than 5 Watts, and the total energy could exceed 45 Joules. Likewise, using a shorter or smaller electrode pair would require scaling the average power down, and the total energy could be less than 4 Joules. The power and duration are calibrated to be less than enough to cause severe damage, and particularly less than enough to ablate diseased tissue 48 within a blood vessel.

In some embodiments the delivery of the drug and gentle heat may be accompanied by balloon angioplasty using gentle dilation to remodel the artery with dilation pressures which are at or significantly lower than standard, unheated angioplasty dilation pressures. Where balloon inflation pressures of 10-16 atmospheres may, for example, be appropriate for standard angioplasty dilation of a particular lesion, modified dilation treatments combined with appropriate electrical potentials (through flexible circuit electrodes on the balloon, electrodes deposited directly on the balloon structure, or the like) described herein may employ from 10-16 atmospheres or may be effected with pressures of 6 atmospheres or less, and possibly as low as 1 to 2 atmospheres. Such moderate dilations pressures may (or may not) be combined with one or more aspects of the tissue characterization, tuned energy, eccentric treatments, and other treatment aspects described herein for treatment of diseases of the peripheral vasculature.

Covalently Bound BioMolecules

Current endovascular therapies for preventing or permanently removing hyperplastic neointima are not completely efficacious. While removal of such tissue is achieved by multiple such therapies, regrowth of the tissue is a frequent occurrence, leading to restenosis and dysfunctional blood flow. Drug-eluting stents are able to inhibit the frequency of restenosis, but fall short of completely restoring vascular function, owing to the presence of a persistent implant; the stent.

More recently, drug clotting balloons have shown an even greater reduction in the frequency of restenosis than drug eluting stents and are removed after treatment, however, high pressure inflation is required to optimally deliver the anti-proliferation/anti-inflammatory biomolecules. The molecules may function to prevent restenosis by preventing inflammatory cell influx (chemo taxis), cell proliferation. The molecules may also function to stabilize the IEL matrix by providing structural support, thus "setting" the lumen diameter.

Figure 9A:
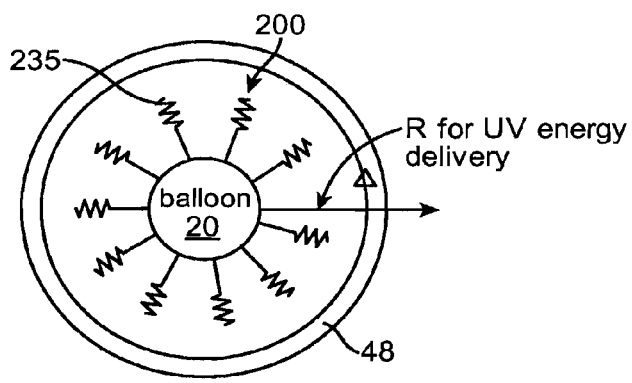
FIGS. 9A and 9B schematically illustrate cross-sectional views showing tissue treatment using biomolecules having a thermally releasable active portion and an inert portion coupled by covalent bond to a balloon surface.
Figure 9B:
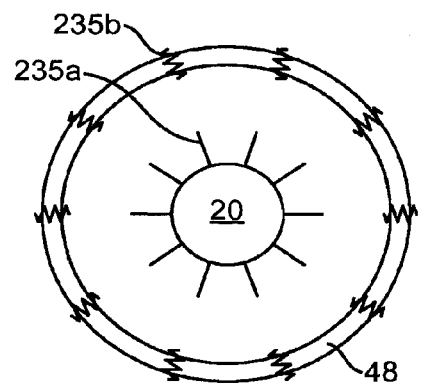

FIGS. 9A and 9B show another embodiment of a catheter system 200 for drug delivery to a body tissue 248. The system 200 is similar to system 10 above, except the use of biomolecules 235 coupled to the balloon 20 instead of a coating. The biomolecules 235 include a thermally releasable active portion 235a and an inert portion 235b coupled by covalent bond to a balloon 20 surface. The active portion or molecule 235b is capable of treating the desired tissue 248, which may be enhanced with temperature or pressure. The inert portion 235a of the biomolecule stays on the balloon. The embodiment described herein utilizes a radiofrequency endovascular balloon catheter that, upon low pressure inflation and energy delivery from the balloon to the atherosclerotic lesion, hyperthermally releases the active portion of the biomolecule that is covalently bound to the balloon, thus, delivering the active portion of the molecule to the targeted tissue. The energy may also include ultrasound emitting energy. The active molecule 235b functions to prevent production of hyperplastic tissue by any means, including, but not limited to, cytostasis (prevention of mitosis), receptor maturation (i.e., those receptors at/on cells on the targeted tissue that are adhesive to/for a chemotactic to/for infiltrating cells that promote hyperplastic tissue formation.

The molecule's bioactive portion 235b is released from the intact biomolecule 235 by delivery of energy (such as from electrodes 34) that induces a local hyperthermia environment. The molecule is stable under the hyperthermia conditions. The molecule can prevent one or all of the following functions:
cell proliferation:
cell function:
receptor-ligand binding:
chemotaxis of inflammatory cells to the target tissue and migration of cells in the native artery strata to the diseased tissue.

The influx of the molecule 235b into the diseased tissue 48 is facilitated and/or hastened by the energy mediated hypothermia, i.e., cleavage from the intact biomolecule, migration into the diseased tissue, and residence in the diseased tissue by virtue of increased porosity are all accelerated by the hyperthermia.

This invention uniquely delivers a bioactive molecule into diseased tissue with:
greater speed, by hypothermal acceleration:
more completeness, by rendering the diseased tissue more receptive/porous to the molecule: and/or
with no inactive segments of the biomolecule, i.e., no polymer, inactive protein sequence/segment, or co-factors required for activation left at the treatment site (the inactive segments stay on the balloon).

Clinical application and uses are designed to reduce plaque, inhibit restenosis in stented or not-stented site, and may be used as an adjunctive treatment to aggressive non-implantable endovascular procedures and stent implants.

Fluid Delivery Channels

Figure 7:
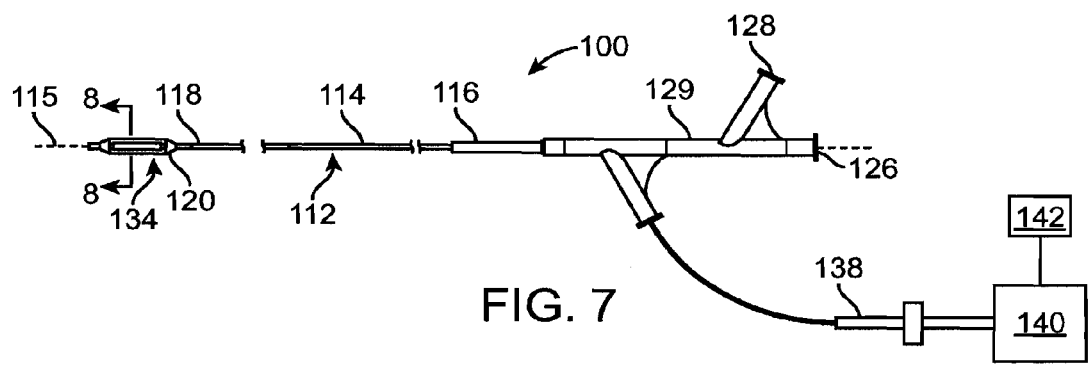
FIG. 7 schematically illustrates another embodiment of a catheter system having fluid delivery channels for selective fluid delivery to a body tissue being disposed about a lumen.

FIG. 7 shows another embodiment of a catheter system 100 having fluid delivery channels for selective fluid delivery to a body tissue being disposed about a lumen. The catheter system 100 includes a balloon catheter 112 having a catheter body 114 with a proximal end 116 and a distal end 118. Catheter body 114 is flexible and defines a catheter axis 115, and may include one or more lumens, such as a guidewire lumen 122 and an inflation lumen 124. Catheter 112 includes an inflatable balloon 120 adjacent distal end 118 and a housing 129 adjacent proximal end 116. Housing 129 includes a first connector 126 in communication with guidewire lumen 122 and a second connector 128 in fluid communication with inflation lumen 124. Inflation lumen 124 extends between balloon 120 and second connector 128. Both first and second connectors 126, 128 may optionally comprise a standard connector, such as a Luer-Loc™ connector. A distal tip may include an integral tip valve to allow passage of guidewires, and the like.

Housing 129 also accommodates an electrical connector 138. Connector 138 includes a plurality of electrical connections, each electrically coupled to electrodes 134 via conductors 136. This allows electrodes 134 to be easily energized, the electrodes often being energized by a controller 140 and power source 142, such as RF energy, microwave energy, ultrasound energy, or other suitable energy sources. In one embodiment, electrical connector 138 is coupled to an RF generator via a controller 140, with controller 140 allowing energy to be selectively directed to electrodes 134 or electrode pairs. Controller 140 may include a processor or be coupled to a processor to control or record treatment.

Figure 8A:
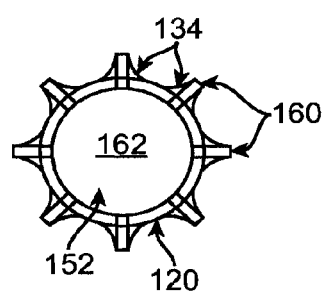
FIG. 8A schematically illustrates a cross-section and FIG. 8B is an enlarged section of the balloon in FIG. 7 showing fluid delivery channels through the balloon coupled to electrodes mounted on a surface of the balloon.
Figure 8B:
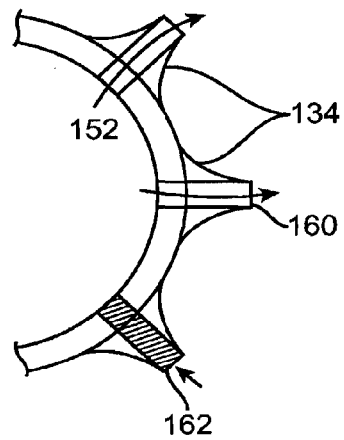

FIG. 8A shows a cross-section of the balloon 120 and FIG. 8B is an enlarged section showing fluid delivery channels 160 through the balloon 120 coupled to electrodes 134 mounted on a surface of balloon 120. Electrodes 134 include associated conductors extending proximally from the electrodes. Electrodes 134 and fluid delivery channels 160 may be arranged in many different patterns or arrays on balloon 120. Fluid delivery channels 160 may be coupled to a fluid reservoir or lumen 162 holding the fluid 152. In some embodiments, the inflation medium may contain the fluid to be delivered. In some embodiments, the channels 160 thru balloon 120 may be filled with wax-like material 164 that can be expelled thermally in order to open the channel (or any other material that can be expelled). In other embodiments, electrodes 134 may open and close a flap to release the fluid.

The delivery channels 160 may protrude from the balloon surface such that they are capable of penetrating the body tissue of the lumen. In some embodiments, the electrodes may penetrate the body tissue.

The catheter system 100 may also include a tissue analyzer configured to characterize the body tissue. In some embodiments, electrodes 134 may be sensing electrodes, as discussed above, that could help characterize the tissue to identify regions the be treated or not using electrical impedance tomography. Other characterization, such as intravascular ultrasound, optical coherence tomography, or the like may be used to identify regions to be treated. Electrodes 134 may be energized in response to the characterized body tissue.

Some embodiments described herein may be used to treat atherosclerotic disease by selective fluid delivery in combination with "gentle heating" to further enhance the fluid delivery or treatment, as discussed above.

Electrodes 134 may be selectively energized to open or close fluid delivery channels 160 to treat tissue. One method includes opening the fluid delivery channels 160 by selectively heating the electrodes (by Joule heating or other means, including inducing a heightened temperature in the adjacent region, whereby hear transfer could heat the electrode(s)), such that a material 164, that would otherwise block the channel, is phase changed from solid to liquid. Another possible method may include the use of MEMS (micro-electormechanical-systems) to open and/or close channels 160 selectively.

In some embodiments, the fluid delivery channels may be vias through the electrodes (perfused electrodes). The vias or small holes may be used to deliver a fluid to the artery tissue proximate the electrode. The holes may be less than 1 µm in diameter and may be made with a laser or ion beam. The holes may be made in the electrodes and balloon. In one example, electrode pads on a flexible circuit are designed with vias that are plated. The flexible circuit is mounted on a balloon and a laser or ion beam is used to create the holes in the flexible substrate and balloon. There may be several holes in the flexible/balloon for every electrode pad. The balloon may then be perfused with standard perfusion balloon equipment or specialized equipment. This perfusion approach may also provide additional advantages beyond fluid delivery, such as eliminating sticking, carry away heat or regulate the impedance of the load.

In some embodiments, a porous balloon may be used having fluid delivery channels on a micro-level, allowing select molecules through with the addition of heat. The porous balloon may have an inner layer, a porous outer layer or membrane, drug or fluid molecules positioned between the layers (i.e., a reservoir) and electrodes coupled to the outer layer. At low pressures, the molecules stay within the reservoir. As heat is applied, the molecules may go through the porous layer, which may be done in different ways. For example, as the heat is applied, the drug molecules may become exited, providing enough force to go through the porous outer layer. In another example, as heat is applied to the balloon, the pores expand, allowing the drug molecules to go through the porous outer layer. The molecules may also pass through the porous outer layer or membrane by osmotic pressure along with the heat.

In some embodiments, the treatments may include a drug, and/or thermal, and/or small or large molecules injection, and/or RF, and/or balloon dilatation, and/or hyperthermia.

While the devices, systems, and methods disclosed herein discuss a balloon as the radially expandable structure, other expandable structures may also be used, such as described in U.S. patent application Ser. No. 11/975,651, the full disclosure of which is incorporated herein by reference.

Thermally Excited Ozmolarity

In some embodiments, a porous balloon may be used having fluid delivery channels on a micro-level in a membrane, allowing molecules through with the addition of pressure and heat. The concept delivers a fluid or drug to a specific site by passing it through the membrane, much like reverse osmosis. In reverse osmosis, a pressure is used to drive a liquid, such as water, through a membrane with passages so small that only the appropriate molecules can pass through. In this embodiment, the membrane barrier retains a drug, like paclitaxel. At low pressures, the drug molecules are not able to pass through the membrane. To release the drug through the membrane, pressure is applied to the drug molecules using a balloon the release of the drug is the accelerated by applying energy locally by an electrode pair or monopolar electrode.

Figure 10:
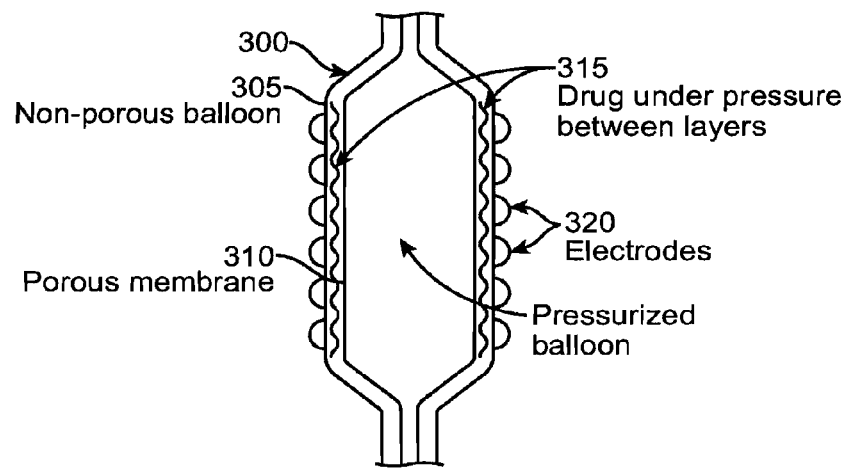
FIG. 10 schematically illustrates another embodiment of a balloon having a membrane for selective drug delivery to a body tissue being disposed about a lumen.

FIG. 10 shows one embodiment of a catheter system, similar to catheter system 10, having a balloon 300 with a nonporous inner balloon 305 (to provide pressure), a porous outer layer, membrane or sleeve 310, a drug or fluid 315 positioned between inner balloon 305 and membrane 310 (i.e., a reservoir), and electrodes 320 coupled to the membrane 310. Electrodes 320 may be similar to the electrodes describe above.

In use, the balloon is placed at the desired tissue site and the balloon is inflated to a suitable pressure, such as 4-6 ATM. When the electrodes are energized, the heat energy causes the membrane pores to open and the drug molecule to excite and make their way through the pores to the tissue.

The devices, systems, and methods disclosed herein may be used to selectively deliver fluid in any artery, for example, the femoral, popliteal, coronary and/or carotid arteries. While the disclosure focuses on the use of the technology in the vasculature, the technology would also be useful for any luminal obstruction. Other anatomical structures in which the present invention may be used are the esophagus, the oral cavity, the nasopharyngeal cavity, the auditory tube and tympanic cavity, the sinus of the brain, the arterial system, the venous system, the heart, the larynx, the trachea, the bronchus, the stomach, the duodenum, the ileum, the colon, the rectum, the bladder, the ureter, the ejaculatory duct, the vas deferens, the urethra, the uterine cavity, the vaginal canal, and the cervical canal.

The devices, systems, and method disclosed herein may employ one or more of a wide variety of mechanisms to facilitate, promote, and/or enhance transport of at least one drug from a fluid, gel, or solid of a catheter (or other delivery structure) toward, to and/or into a desired treatment site or tissue. Exemplary thermally-mediated drug transport mechanisms which may be employed are described above. Additional mechanisms may also be used including electrically mediated drug transport mechanisms, optionally including mechanisms such as electroporation, iontophoresis, and the like. Electroporation may allow targeting drug molecules intracellularly via creating passages in the cell membrane. Electroporation can significantly increase the electrical conductivity and permeability of the cell plasma membrane by application of an external electrical field, optionally by application of an electroporation voltage (which may involve a series of electroporation potentials) using one or more electrodes of the balloon catheters described herein. Iontophoresis may be employed by applying a relatively small electric potential so as to deliver a medicine or other chemical through the luminal surface, with the electrical potential again optionally being applied using one or more electrodes of the balloon catheters described hereinabove. As another example, anti-inflammatory molecules could be delivered via iontophoretic membranes to atherosclerotic lesions. Small molecule inhibitors of inflammation, thrombogenesis, and thrombosis can be delivered to atherolosclerotic lesions via iontophoretic methods using devices and systems described herein to slow or prevent progression of atherosclerosis and thrombus formation. Examples of suitable inflammatory and/or thrombogenic tissue targets in the artery may include platelet cell adhesion factor (PECAM), Tissue Factor (TF), matrix metalloproteinases (MMP), and/or the like. Examples of a small molecule anti-inflammatory/anti-thrombosis therapeutics that would be amenable to delivery via iontophoresis may include heparin, heparin sulfate, and/or the like. Advantageously, suitable potentials may be applied in either a bipolar arrangement (between electrodes of the balloon catheter) or in a monopolar mode. Suitable potentials may be applied by commercially available iontophoresis or electroporation systems, or specialized potential generators may be employed. These drug transport mechanisms can optionally be combined, for example, with a thermal mechanism used (for example, by energizing electrodes so as to heat a coating, and optionally to facilitate release of a drug and thermally enhance movement of the drug into a target tissue), followed with an electrically mediated drug transport mechanism (optionally by energizing the same electrodes or different electrodes of the balloon with a suitable potential).

While the exemplary embodiments have been described in some detail, by way of example and for clarity of understanding, those of skill in the art will recognize that a variety of modification, adaptations, and changes may be employed. Hence, the scope of the present invention should be limited solely by the appending claims.

What is claimed is:
1. A medical device, comprising:
 a catheter shaft having a distal region;
 an expandable member coupled to the distal region;
 a coating disposed along the expandable member, the coating including a releasable drug;
 a plurality of electrodes coupled to the expandable member;
 wherein the plurality of electrodes includes one or more pairs of bipolar electrodes; and
 wherein the electrodes are configured to induce a phase change in the coating and release the releasable drug from the coating.

2. The medical device of claim 1, wherein the expandable member includes a balloon.

3. The medical device of claim 2, wherein the electrodes are mounted to an outer surface of the balloon.

4. The medical device of claim 2, wherein the balloon is configured to be fully inflated with a pressure of 6 atmospheres or less.

5. The medical device of claim 2, wherein the balloon is configured to be fully inflated with a pressure of 1 to 2 atmospheres.

6. The medical device of claim 1, further comprising a generator coupled to the catheter shaft for selectively energizing the plurality of electrodes.

7. The medical device of claim 6, wherein the generator is configured to energize the electrodes for 1 to 180 seconds.

8. The medical device of claim 6, wherein the generator is configured to energize the electrodes with 0.25 to 5 Watts average power.

9. The medical device of claim 6, wherein the generator includes an RF energy source.

10. The medical device of claim 1, wherein at least some of the plurality of electrodes are configured to sense impedance.

11. The medical device of claim 1, wherein at least some of the plurality of electrodes are configured to characterize target tissue based on sensed impedance.

12. The medical device of claim 1, wherein the coating has coating melting temperature above 37° Celsius.

13. The medical device of claim 1, wherein energizing the electrodes liquefies at least a portion of the coating.

14. A medical device, comprising:
 a catheter shaft having a distal region;
 a balloon coupled to the distal region;
 a coating disposed on the balloon, the coating including a releasable drug;
 one or more pairs of bipolar electrodes coupled to the balloon;
 wherein the electrodes are configured to induce a phase change in the coating and release the releasable drug from the coating, wherein the phase change of the coating from a solid to a liquid releases the drug; and
 a generator coupled to the catheter shaft, the generator being configured to selectively energize the electrodes.

15. The medical device of claim 14, wherein the generator includes an RF energy source.

16. The medical device of claim 14, wherein at least some of the one or more pairs of bipolar electrodes are configured to sense impedance and characterize target tissue based on sensed impedance.

17. The medical device of claim 14, wherein the coating has coating melting temperature above 37° Celsius.

18. The medical device of claim 14, wherein energizing the electrodes liquefies at least a portion of the coating.

19. A medical device, comprising:
 a catheter shaft having a distal region;
 a balloon coupled to the distal region;
 a thermally changeable coating disposed on the balloon, the coating including a releasable drug;
 wherein the thermally changeable coating has a coating melting temperature above 37° Celsius;

one or more pairs of bipolar electrodes coupled to the balloon;

wherein the electrodes are configured to heat the coating above the coating melting temperature so as to at least partially liquefy the coating and release the releasable drug from the coating; and a generator coupled to the catheter shaft, the generator being configured to selectively energize the electrodes.

* * * * *